United States Patent
Ji et al.

(10) Patent No.: US 9,462,948 B2
(45) Date of Patent: Oct. 11, 2016

(54) SET-TOP BOX FOR MONITORING TELEHEALTH SENSORS

(75) Inventors: Lusheng Ji, Randolph, NJ (US); Robert R. Miller, II, Convent Stn., NJ (US)

(73) Assignee: AT&T INTELLECTUAL PROPERTY I, L.P., Atlanta, GA (US)

(*) Notice: Subject to any disclaimer, the term of this patent is extended or adjusted under 35 U.S.C. 154(b) by 700 days.

(21) Appl. No.: 13/034,086

(22) Filed: Feb. 24, 2011

(65) Prior Publication Data
US 2012/0218123 A1    Aug. 30, 2012

(51) Int. Cl.
| | |
|---|---|
| G08C 19/22 | (2006.01) |
| H04Q 9/00 | (2006.01) |
| G06Q 10/00 | (2012.01) |
| G06Q 50/00 | (2012.01) |
| A61B 5/00 | (2006.01) |
| G06F 19/00 | (2011.01) |
| A61B 5/021 | (2006.01) |
| A61B 5/024 | (2006.01) |
| A61B 5/11 | (2006.01) |
| A61B 5/145 | (2006.01) |

(52) U.S. Cl.
CPC ......... *A61B 5/0022* (2013.01); *G06F 19/3418* (2013.01); *A61B 5/021* (2013.01); *A61B 5/02438* (2013.01); *A61B 5/112* (2013.01); *A61B 5/14532* (2013.01); *A61B 5/6804* (2013.01); *A61B 5/6898* (2013.01); *A61B 5/7232* (2013.01); *A61B 5/742* (2013.01)

(58) Field of Classification Search
None
See application file for complete search history.

(56) References Cited

U.S. PATENT DOCUMENTS

| | | | |
|---|---|---|---|
| 7,835,926 B1* | 11/2010 | Naidoo ................ | A61B 5/0002 705/2 |
| 8,027,668 B2* | 9/2011 | Behzad et al. ............. | 455/414.3 |
| 2008/0088436 A1* | 4/2008 | Reeves et al. ........... | 340/539.12 |
| 2008/0129465 A1* | 6/2008 | Rao ........................... | 340/286.02 |
| 2008/0146892 A1* | 6/2008 | LeBoeuf ................. | A61B 5/11 600/300 |
| 2008/0154009 A1* | 6/2008 | Johnstone ............. | A01F 15/071 526/348.1 |
| 2008/0154099 A1* | 6/2008 | Aspel .................. | G06F 19/3418 600/301 |
| 2008/0300917 A1* | 12/2008 | Ryan ................... | G06F 19/3418 705/2 |
| 2010/0121157 A1* | 5/2010 | Espina et al. ................. | 600/301 |
| 2010/0122220 A1* | 5/2010 | Ainsworth ........ | G06F 17/30899 715/866 |
| 2010/0201512 A1* | 8/2010 | Stirling et al. ........... | 340/539.11 |

* cited by examiner

*Primary Examiner* — Firmin Backer
*Assistant Examiner* — Jerold Murphy
(74) *Attorney, Agent, or Firm* — Amin, Turocy & Watson, LLP

(57) ABSTRACT

The subject disclosure provides a system and method for a set-top box for monitoring telehealth and biometric sensors. A subject patient is associated with telehealth and biometric sensors which measure the subject patient's vital signs and other health related attributes. In one aspect, the system includes a set-top box for continuously gathering biometric and telehealth sensor data. The set-top box includes a sensor interface for interfacing with the sensors and supports wireless and wired connections to the sensors. The system additionally may include a system management station for providing feedback to the subject patient.

20 Claims, 12 Drawing Sheets

SET-TOP BOX FOR MONITORING TELEHEALTH SENSORS

TECHNICAL FIELD

The subject disclosure relates generally to remote monitoring and connectivity for a sensor network, and more specifically, to a console for health management sensor network with communication ability for monitoring purposes.

BACKGROUND

For most chronic diseases such as cancer, heart disease, asthma, AIDS, diabetes, or hypertension, patients generally receive medical suggestions for periodic return clinical visits (such as every four to twelve weeks). The severity of these diseases may increase or decrease before they see the medical provider. However, periodic outpatient clinical services or long-period prescription can only provide passive defenses, instead of active controlling by doctors or medical hospital for any possible serious situation of the patient.

Further, outpatient services cannot distribute medical resources efficiently. Some chronic diseases, (e.g., asthma) are largely influenced by environmental factors. These factors including, e.g., change of atmospheric temperature, weather moisture, or the amount of pollutant, may cause acute exacerbation of asthma or even respiratory distress. However, given the outpatient nature of treatment for such chronic diseases, doctors or the hospitals are often unable to provide immediate aid in the event of an unforeseen health emergency.

While, home care visits and emergency medical services are available to care for the chronic disease patients, such services are generally very costly. In an effort to reduce some of the expense, remote healthcare delivery systems have also been implemented. For example, telemedicine has been around since the 1970s and refers to health care delivery where physicians examine distant patients through the use of telecommunications technologies. However, telemedicine has failed to gain significant traction in the marketplace for a variety of reasons, such as a disconnect between patient and technology and poor selection of underlying infrastructure.

BRIEF DESCRIPTION OF THE DRAWINGS

These and other features, aspects, and advantages of the exemplary embodiments are better understood when the following Detailed Description is read with reference to the accompanying drawings, wherein.

DETAILED DESCRIPTION

Overview

Figure 1:
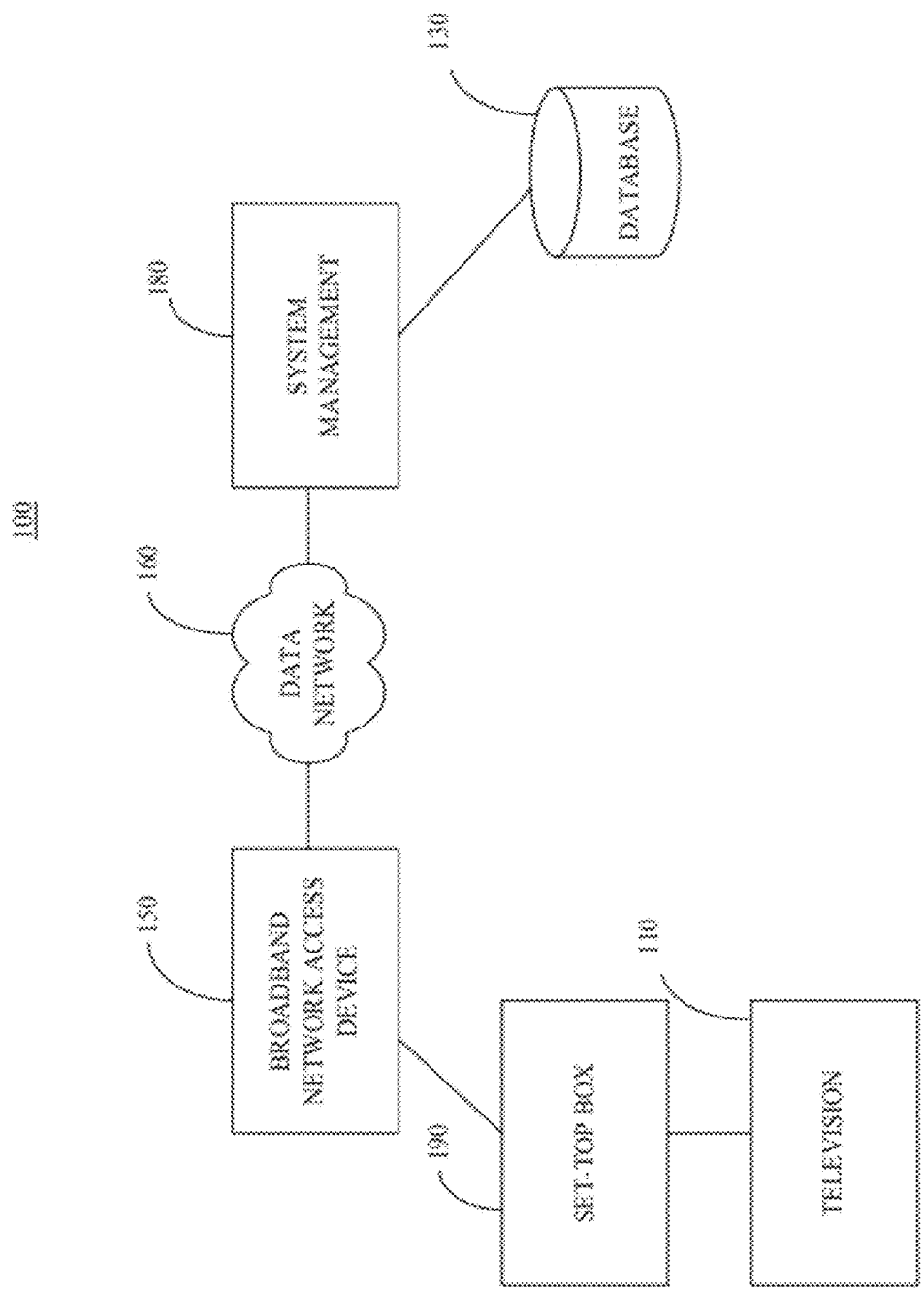
FIG. 1 is a simplified schematic illustrating an operating environment according to exemplary embodiments.

As noted above, certain chronic diseases exist that are treated on an outpatient basis, yet in-home care can be prohibitively expensive, while previous attempts at telemedicine have failed to meet market needs. A related type of remote healthcare delivery system is referred to herein as "telehealth." Similar to previous attempts at telemedicine, telehealth is the use of telecommunication technologies to provide health care services and access to medical and surgical information for training or education for health care professionals or consumers. Thus, telehealth can be directed to increasing awareness or education with respect to health-related issues, or to facilitate medical research across distances.

Telehealth can be implemented through an integrated television-based broadband home health system, which can be particularly advantageous for people adverse to being introduced to new technology. The integrated television-based broadband home health system can be capable of delivering various emergency response, life safety, telemedicine, or remote health monitoring to benefit patients and their families. Remote caregiving services through patient interaction with their television set can provide patients with interaction through a familiar piece of home equipment while taking advantage of the two-way digital communication capability of the modern set-top box. Employing set-top boxes can provide an ideal interface for remote monitoring and connectivity for healthcare related communication.

To these and other related ends, this disclosure describes a system and method for a set-top box for monitoring telehealth and biometric sensors. In one aspect, the system for monitoring telehealth sensors, can include: a network interface for connecting to a data network. Furthermore, the system can include a sensor interface coupled to the network interface. Hence, the sensor interface can be configured to interface with at least one telehealth sensor for gathering biometric data from the at least one telehealth sensor. In addition, the system can include an intelligent component for monitoring data gathered from the at least one telehealth sensor, wherein the intelligent component associates the data from the at least one telehealth sensor with a subject and wherein the intelligent component transmits the data from the at least one telehealth sensor through the network interface.

In one or more aspect, a method includes employing a processor to execute a set of code instructions stored in a computer-readable storage medium, the set of code instructions, when executed by the at least one processor, performs a group of acts comprising: interfacing with at least one telehealth sensor; substantially continuously collecting biometric data from the at least one telehealth sensor; associating the biometric data from the at least one telehealth sensor with a subject; and transmitting the biometric data from the at least one telehealth sensor through a network interface.

In one or more aspect, a system for monitoring telehealth sensors can include a database engine for receiving biometric data from a wireless transceiver and providing real-time feedback, wherein the database engine is coupled to a wireless transceiver via at least one wireless communication network. Furthermore, the wireless transceiver can be coupled to at least one sensor for substantially continuously gathering the biometric data from a telehealth sensor associated with a subject. Advantageously, the biometric data can be associated with the body movements of the subject and the real-time feedback can be associated with the biometric data from the subject.

Monitoring Telehealth Sensors

One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details, e.g., without applying to any particular networked environment or standard. In other instances, well-known structures and devices are shown in block diagram form in order to facilitate describing the embodiments in additional detail.

As used in this application, the terms "component," "module," "system," "interface," "platform," "station," "framework," "connector," or the like are generally intended to refer to a computer-related entity, either hardware, a combination of hardware and software, software, or software in execution or an entity related to an operational machine with one or more specific functionalities. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. As another example, an interface can include I/O components as well as associated processor, application, and/or API components.

Further, the various embodiments can be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications can be made to this configuration without departing from the scope or spirit of the various embodiments.

In addition, the words "exemplary" and "example" are used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, terms like "user equipment," "mobile station," "mobile," subscriber station," "access terminal," "terminal," "handset," "end device," "mobile device," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "base station," "Node B," "evolved Node B," "home Node B (HNB)," and the like, are utilized interchangeably in the subject application, and refer to a wireless network component or appliance that serves and receives data, control, voice, video, sound, gaming, or substantially any data-stream or signaling-stream from a set of subscriber stations. Data and signaling streams can be packetized or frame-based flows.

Furthermore, the terms "user," "subscriber," "customer," and the like are employed interchangeably throughout the subject specification, unless context warrants particular distinction(s) among the terms. It should be appreciated that such terms can refer to human entities or automated components supported through artificial intelligence (e.g., a capacity to make inference based on complex mathematical formalisms), which can provide simulated vision, sound recognition and so forth. In addition, terms "core network", "core mobility network", "service provider network" and the like are employed interchangeably throughout the subject specification, unless context warrants particular distinction(s) among the terms.

Although the term "set-top box" is used extensively in the subject specification, it will be understood that a set-top box encompasses many different types of communication devices. A set-top box may alternatively be referred to as a set top box device, STB, Receivers, Converters, Gateways, Residential Gateways, Decoders, Intelligent Set-top Boxes, Set-top Decoders, Smart Encoder, Digital TV Converter, DTV Converter, Voice-enabled Set-top Boxes, Digital Decoder, DTV Tuner, IPTV Tuners, Descrambler, Digital Set-top Box, Addressable Converter, Demodulator, Smart TV Set-top Box, ITV enabled Set-top Box, Internet-enabled Set-top Box, ITV enabled Set-top Cable Box, Satellite-enabled Set-top Box, Cable-enabled Set-top Box, Low-end Boxes, Thin Boxes, Thick Boxes, Smart TV Set-top Box, Super Box, All-in-one Set Top Box, Integrated Set Top Box, Hybrid Cable Box, Media Center. Associated with Digital Media Adapters, Digital Media Receivers, Windows Media Extender Set-top Boxes, Gaming Consoles, Multifunction Adapter.

In short, a set-top box ("STB") is a computerized device that processes digital information. STBs come in many forms and can have a variety of functions. Digital Media Adapters, Digital Media Receivers, Windows Media Extender and most video game consoles are also examples of set-top boxes. Currently, the type of TV set-top box most widely used is one which receives encoded/compressed digital signals from the signal source (perhaps at the cable provider or telephone company TV provider's headend) and decodes/decompresses those signals, converting them into analog or digital signals that the television can understand. The STB also accepts commands from the user (often via the use of remote devices such as a remote control) and transmits these commands back to the network operator through a return path. Most set-top boxes deployed today have return path capability for two-way communication.

Referring to the drawings, FIG. 1 is a schematic block diagram of an example system for monitoring of healthcare sensors. The integrated home healthcare system 100 includes a broadband network access device 150, a set-top box 190, and a television 110 coupled together by a data network 160, for example, the Internet or an interactive television network (e.g., an Internet Protocol Television or IPTV network). The system further includes a system management station 180 coupled together with a database 130 for monitoring of a subject patient (not shown). The system management station 180 is also configured to provide various home health services to a subject patient located remotely from the system management station through the data network 160. Of course, it is further contemplated that the system for monitoring of healthcare sensors may be configured to include additional system management stations. The additional system management stations may be used to provide additional home health services such as monitoring by specialist physicians, ambulatory service providers, emergency medical personnel, nurse practitioners, and so forth. It is further contemplated that such additional provider and/or system management stations may be used to provide backup home health services to a subject patient and/or management services for the integrated television-based broadband home health system. It is further contemplated that such additional provider and/or system management stations may be used by medical service providers and/or family members of the subject patient to periodically monitor various characteristics of the subject patient in order to, e.g., periodically "check up" on the subject patient.

The system management station 180 may be a healthcare provider station where healthcare professionals are available to provide home healthcare services to patients remotely located. Generally, the system management station 180 would be located at either a physician's office or a healthcare agency or other type of organization responsible for providing home health services to patients at remotely located patient stations. In the case of a physician's office the system management station would typically be comprised of a computer system, for example, a personal computer ("PC") having a plurality of peripheral devices coupled thereto. Software residing on the PC should include an Internet browser, for example, Microsoft Explorer, video conferencing software, for example, Microsoft NetMeeting, and any software applications needed for communicating with the subject patient. The software residing on the PC may also include various displays and interfaces so that raw medical data received from the patient may be analyzed, archived, or collected.

Figure 2:
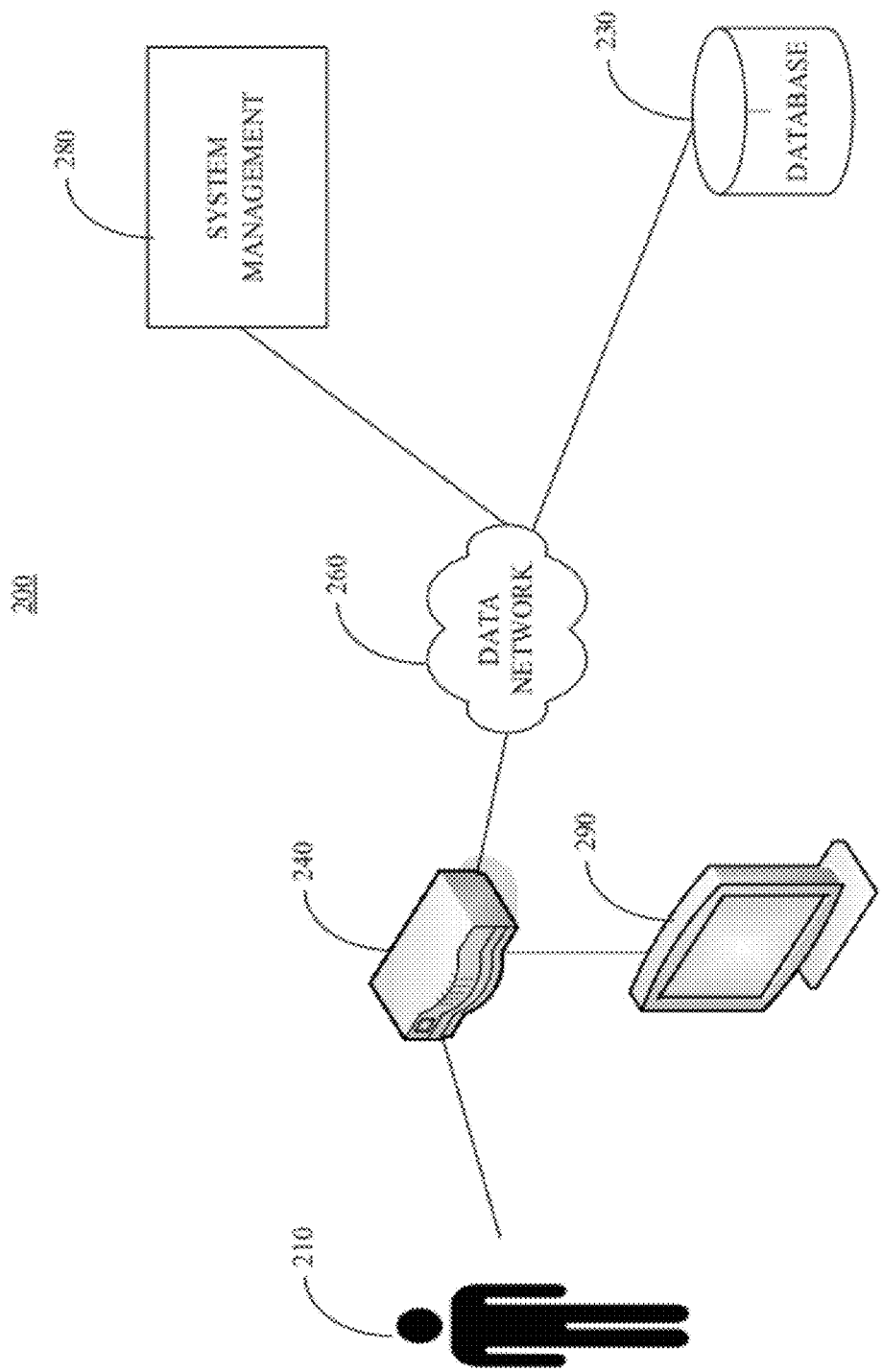
FIG. 2 is a simplified schematic illustrating an operating environment according to exemplary embodiments.

Referring to the drawings, FIG. 2 illustrates an example system 200 for processing data from various biometric and biomechanical sensors associated with the subject patient 210. The subject patient 210 has various biometric and biomechanical sensors (not shown) positioned on the subject's body. In one aspect, the subject patient 210 is associated with various devices that can measure various health related attributes associated with the subject patient 210. For example, a scale for measuring the body weight of a subject may be associated with the subject patient for reporting the body weight of a subject. As another example, a prescription medication dispensing device can report the subject patient's compliance with a physician's instructions for following the precise dosages and/or frequency of the medications prescribed to the subject patient.

The sensors may be attached to the subject's clothing or shoes or may be woven or positioned with the subject's clothing or shoes. In one aspect, the sensors can be associated with joints or appendages of the body in order to track position and/or movement of such joints or appendages. The sensors can gather data relating to various physical characteristics, positions, changes, performance, or properties of the subject. Such data can be referred to as "biometric" data. Biometric data can include biomedical or biomechanical data, and can include any of the following: data tracing the trajectory, speed, acceleration, position, force/pressure exerted by or experienced by the body, orientation, etc. of a subject's appendage or other body part; data showing the heart rate, blood pressure, temperature, stress level, moisture content, toxin level, viability, respiration rate, etc. of a subject; data showing whether or not a subject is performing a signal or communication movement (e.g., teeth closed, arm cocked, etc.); data showing the posture or other status of a subject (e.g., prone or erect, breathing or not, moving or not); data showing the emotional state of a subject; etc. For example, the sensors can track movement of the subject and/or tension in the subject's muscles. In some aspects, the sensors can include one or more of the following technologies: accelerometer technology that detects accelerations; gyroscope technology that detects changes in orientation; compass or magnetic technology that senses position and/or alignment with relation to magnetic fields; satellite-based; "GPS"-style technology; gait or stride instabilities or impact points; radio-frequency technology, etc. In summary, the subject patient 210 represents the patient as well as his or her attributes that are identifiably associated with the subject patient.

The sensors associated with the subject patient communicate with a set-top box 240. In one aspect, the set-top box 240 can collect and store data (e.g., analog and/or digital data) from the sensors associated with the subject patient 210. In one aspect, the data is converted from analog to digital in the sensors or the set-top box to facilitate storage and/or transmittance. In another aspect, the data is sequenced, coded, and or separated to make the reception, storage, and/or transmission more efficient through compression of the data or the like. In some aspects, the set-top box 240 can be a mobile device, a cell phone, smartphone, personal digital assistant (PDA), pocket PC, tablet PC, MP3 player, or other portable communications and/or computing device. The mobile device may be a disposable cell phone or a prepaid cell phone.

The set-top box 240 also transmits analog/digital signals to the television 290. Generally the set-top box receives encoded/compressed digital signals from the signal source (perhaps at the cable provider or telephone company TV provider's headend) and decodes/decompresses those signals, converting them into analog or digital signals the television can understand. The STB also accepts commands from the user (often via the use of remote devices such as a remote control) and transmits these commands back to the network operator through a return path. Most set-top boxes deployed today have return path capability for two-way communication.

The set-top box 240 transmits signals through a data network such as the Internet 260. Coupled to the data network is a system management station 280 and a database 230 for monitoring the subject patient 210. The system management station 280 is also configured to provide various home health services to a subject patient located remotely from the system management station through the data network 260. In one aspect, it is contemplated that the system for monitoring of healthcare sensors can be configured to include additional system management stations. The additional system management stations may be used to provide additional home health services such as monitoring by specialist physicians, ambulatory service providers, emergency medical personnel, nurse practitioners, and so forth. It is further contemplated that such additional provider and/or system management stations may be used to provide backup home health services to a subject patient and/or management services for the integrated television-based broadband home health system. It is further contemplated that such additional provider and/or system management stations may be used by medical service providers and/or family members of the subject patient to periodically monitor various characteristics of the subject patient in order to periodically "check up" on the subject patient.

The system management station may be a healthcare provider station where healthcare professionals are available to provide home healthcare services to (remotely located) patients. Generally, the system management station 280 would be located at either a physician's office or a healthcare agency or other type of organization responsible for providing home health services to patients at remotely located patient stations. In the case of a physician's office the system management station would typically be comprised of a computer system, for example, a personal computer ("PC") having a plurality of peripheral devices coupled thereto. Software residing on the PC should include an Internet browser, for example, Microsoft Explorer, video conferencing software, for example, Microsoft NetMeeting, and any software applications needed for communicating with the subject patient. The software residing on the PC may also include various displays and interfaces so that raw medical data received from the patient may be analyzed, archived, or collected.

Figure 3:
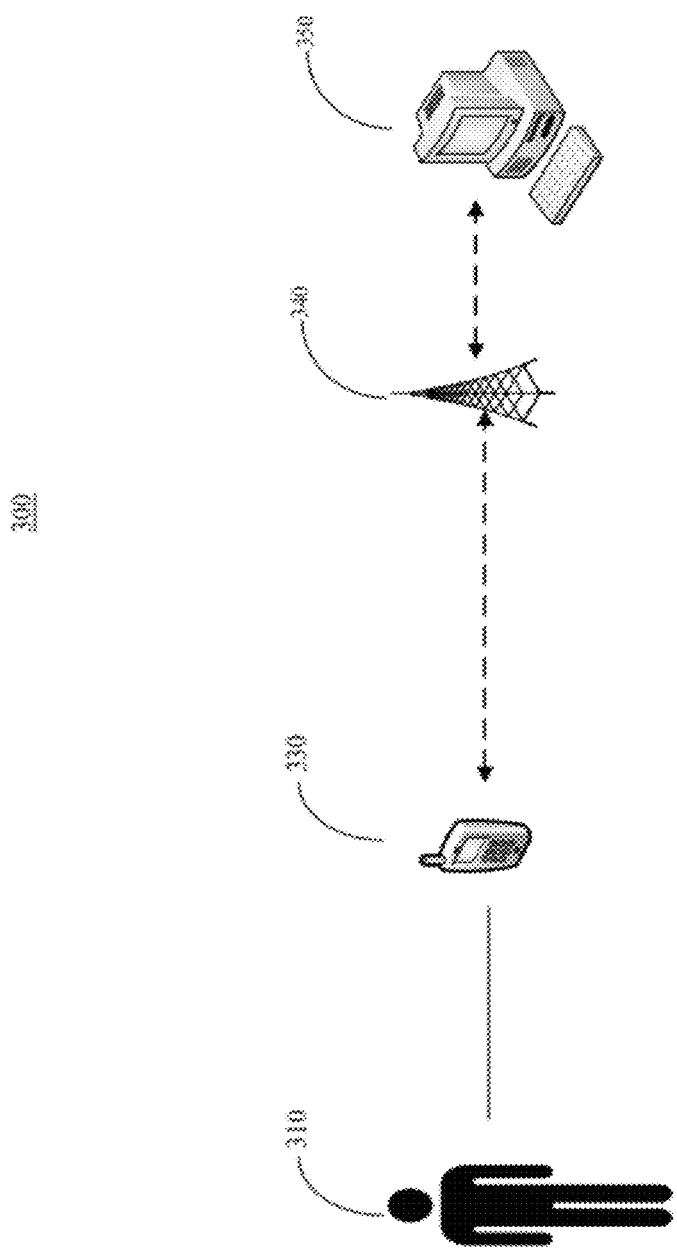
FIG. 3 is a simplified schematic illustrating an operating environment according to exemplary embodiments.

FIG. 3 illustrates another aspect of a system 300 in accordance with an exemplary embodiment. The system 300 illustrates a subject patient 310 having various biometric and biomechanical sensors (not shown) positioned on the subject's body. In one aspect, the subject patient is associated with various devices which may measure various health related attributes associated with the subject patient. For example, a scale for measuring the body weight of a subject may be associated with the subject patient for reporting the body weight of a subject. As another example, prescription medication dispensing device may report the subject patient's compliance with a physician's instructions for following the precise dosages and/or frequency of the medications prescribed to the subject patient.

The sensors may be attached to the subject's clothing or shoes or may be woven or positioned with the subject's clothing or shoes. In one aspect, the sensors can be associated with joints and appendages of the body in order to track position and or movement of such joints and appendages. The sensors can gather data relating to various physical characteristics, positions, changes, performance, or properties of the subject. This data can be referred to as "biometric" data. Biometric data includes biomedical and biomechanical data, and can include any of the following: data tracing the trajectory, speed, acceleration, position, force/pressure exerted by or experienced by the body, orientation, etc. of a subject's appendage or other body part; data showing the heart rate, blood pressure, temperature, stress level, moisture content, toxin level, viability, respiration rate, etc. of a subject; data showing whether or not a subject is performing a signal or communication movement (e.g., teeth closed, arm cocked, etc.); data showing the posture or other status of a subject (e.g., prone or erect, breathing or not, moving or not); data showing the emotional state of a subject; etc. For example, the sensors can track movement of the subject and/or tension in the subject's muscles. In some aspects, the sensors can include one or more of the following technologies: accelerometer technology that detects accelerations; gyroscope technology that detects changes in orientation; compass or magnetic technology that senses position and/or alignment with relation to magnetic fields; satellite-based; "GPS"-style technology; gait or stride instabilities or impact points; radio-frequency technology, etc. In summary, the subject patient 210 represents the patient as well as his or her attributes that are identifiably associated with the subject patient.

The sensors associated with the subject patient communicate with a mobile device 330. The mobile device 330 can be a cell phone, smartphone, personal digital assistant (PDA), pocket PC, tablet PC, MP3 player, or other portable communications and/or computing device. The mobile device may be a disposable cell phone or a prepaid cell phone.

The mobile device 330 can transmit data to a processor 350 through a data network 340, e.g., provided by wireless communications infrastructure. In some aspects, the data is transmitted wirelessly (using radio frequency transmissions, for example). Various communications protocols can be used, including, for example, Bluetooth, ZigBee, TCP/IP, 802.11b, 802.11a, 802.11g, 802.11e, etc.). In some aspects, a transceiver of the mobile device 330 transmits the data over the internet or over a wired or wireless network.

The processor 350 can be one of or a combination of devices or components. In some aspects, the processor 350 can be a computer and/or remote server such as a laptop computer or computer chip/ASIC, for example. The processor 350 can be configured to receive signals from a transceiver included in data network 340 and can have software that allows a healthcare provider to view or otherwise use the data. In some aspects, the processor 350 can be a mobile device, a cell phone, smartphone, personal digital assistant (PDA), pocket PC, tablet PC, MP3 player, or other portable communications and/or computing device. Therefore, a single portable communications device can be configured to variously collect data from the subject patient 310; store the data in its onboard memory (or on a portable storage such as a memory card), and transmit the data.

In one aspect, the mobile device 330 can collect and store data (e.g., analog and/or digital data) from the sensors associated with the subject patient 310. In one aspect, the data is converted from analog to digital in the sensors or the set-top box to facilitate storage and/or transmittance. In another aspect, the data is sequenced, coded, and or separated to make the reception, storage, and/or transmission more efficient through compression of the data or the like.

Figure 4:
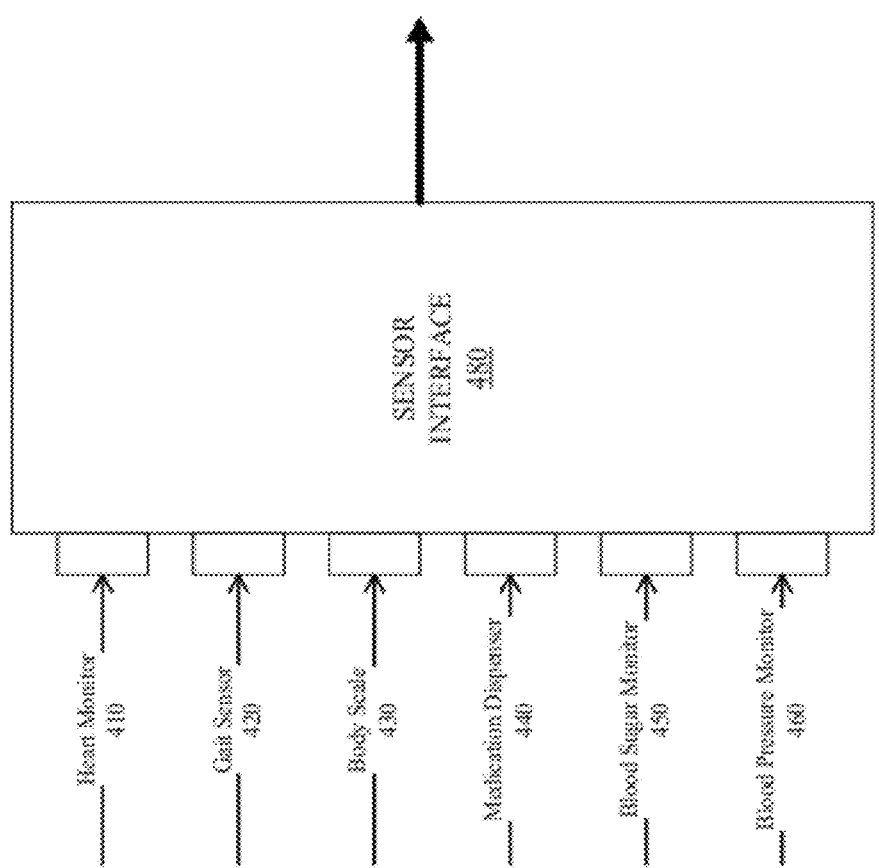
FIG. 4 is a simplified schematic illustrating a sensor interface according to exemplary embodiments.

Referring to FIG. 4, there is shown a schematic illustration of a sensor interface 480 which may be integrated into the set-top box system. The sensor interface 480 can include ports (receptors, receivers, detectors, transceivers) for various biometric or telehealth sensors associated with the subject patient. The ports may be physical ports which can be connected to the various sensors by wires or leads (not shown). Various communication protocols may be used for wired access, including, for example, Universal Serial Bus (USB), proprietary protocols, IEEE 1394 (Firewire), serial binary single-ended standards such as RS-232, SCSI, etc. In a preferred aspect, the ports can gather data from the various sensors by a wireless connection. In some aspects, the data is transmitted wirelessly (using radio frequency transmissions, for example) from the sensors. Various communications protocols can be used, including, for example, Bluetooth, ZigBee, TCP/IP, 802.11b, 802.11a, 802.11g, 802.11e, etc.

As shown in FIG. 4, the sensor interface 480 has a plurality of ports for various biometric sensors. It will be noted that the list of sensors is not meant to be exhaustive but is meant to be illustrative only. The sensor interface 480 includes port 410 for a heart monitor, port 420 for a gait sensor, port 430 for a body scale, port 440 for a medication dispenser, port 450 for a blood sugar monitor, and port 460 for a blood pressure monitor. It will be understood that even though the ports are illustrated as physical ports, the ports may be configured as virtual ports. That is, the ports merely represent the various aspects of the interface for interfacing with the various sensors. Additionally, the ports may be configured for wireless access and/or wired access by the various sensors. In one aspect, the sensor interface 480 may include both wired and wireless access by the sensors. For example, a subject patient with heart disease can be monitored for both heart rate as well as body weight. In that case, the heart rate monitor may transmit real time heart rate data to the sensor interface 480. In addition, a body weight scale that logs and collects body weight data for the subject patient can transmit body weight data to sensor interface 480, either in real time or when periodically coupled to the sensor interface 480, e.g., by a USB connection. The above described examples are meant for illustrative purposes only and are not meant to be limiting.

In another aspect, the sensor interface 480 supports a "store and forward" sensor data collection scheme such that when a subject patient is not within wireless range of the sensor interface 480, the sensor data is collected at the sensor and forwarded to the sensor interface 480 when the subject patient or the sensor is within the wireless range of the sensor interface 480.

A heart rate monitor can be used to monitor and display the subject patient's heart rate. Frequently, subjects use the heart rate monitor to detect the subject's vital signs. The heart rate monitor may also be configured to generate an alarm condition if the subject patient is in an active state and the heart rate exceeds an alarm threshold. Additionally, the heart rate monitor, in conjunction with other biometric sensors may indicate a patient in a distressed state even if the patient is in an inactive state. The heart rate monitor is also useful for patients in an exercising state. If a motion sensor indicates that the patient is standing, and the heart rate exceeds the normal baseline heart rate for that patient's state, the alarm threshold can be reached.

The heart rate monitor is also useful for patients in an exercising state. Walkers can use heart rate to adjust the intensity of their walk, either by speeding up or slowing down to stay in their chosen heart rate zone. It will be noted that two walkers going the same speed may be in different zones according to the attributes of their own physiology so that while one patient is barely working at all, the other might be near maximum and straining. As the patient's fitness improves, one can walk faster at the same heart rate.

As will be discussed below, the most accurate heart rate monitors use a chest strap which fits snugly around the patient's chest just below the breast. A transmitter detects electrical activity of the heart in a similar fashion to an electrocardiogram (ECG). In one aspect, the heart rate monitor may transmit the data representative of the electrical activity to the sensor interface. In another aspect, the heart rate monitor may log the data representative of the electrical activity for later or periodic updating to the sensor interface.

A gait sensor allows for the capturing of a subject's gait pattern. A gait sensor may include a tread plate supported in a frame via an elastic suspension. The gait sensor may be configured to include acceleration sensors such that suspension, motion capture, or performance animation can be monitored. In another aspect, some sensors, such as the gait sensor, can be embedded into the soles of shoes or other footwear. In one or more aspect, the gait sensor detects the subject patient's gait pattern and may indicate a sudden fall or a slip, which can be particularly dangerous for elderly or handicapped patients.

A body weight scale provides periodic measurements of the subject patient's body weight for monitoring the overall fitness of the subject. Obesity in the human race has reached the scale of a global epidemic, with the concomitant adverse health effects now constituting an immediate health crisis. Health problems stemming from inactivity, poor nutritional choices, and other deleterious habits such as smoking, drug and alcohol abuse, are taking an ever increasing toll on the population, with the health care expenses involved, and the cost of lost productivity being on a scale so large that it is more than likely immeasurable by any accurate means. The medical profession, and all of the allied health sciences worldwide associated therewith tend to agree that a balance of physical exercise, sound nutrition and weight management are the keys to good health, especially as it relates to cardiovascular health, and the avoidance of, or the control of diabetic conditions.

A medication dispenser monitors the subject patient's compliance with the medical provider's instructions regarding dosage and frequency of medications prescribed to the subject patient. In one aspect, the medication dispenser keeps an inventory, usually by time released compartments, of various medications. The contents of the medication dispenser may frequently be inventoried in order to determine the type and quantities of medication remaining in the medication dispenser. For example, an inventory of a medication cart may need to be conducted each day. In order to conduct an inventory of a medication dispenser, each drawer or compartment must be individually accessible and the contents of each compartment must be counted. In one aspect, the medication dispenser provides an improved medication cart for permitting the remaining inventory stored within a medication cart to be determined in an efficient manner.

A blood sugar monitor or glucometer is typically used by diabetic patients to monitor their blood glucose levels. A typical glucometer of such design has a blood sample strip-receiving region, into which the user first inserts a disposable test strip and then applies a blood sample for analysis. A display screen on the meter displays the results of the blood glucose analysis. In one aspect, the glucometer can be coupled to a data communication device so that the results of a blood glucose analysis performed and stored by the meter can be reported directly to a monitoring facility that tracks the results and the patient's status.

A blood pressure monitor monitors the subject patient's arterial blood pressure. Blood pressure is a vital sign that is particularly susceptible to false alarms. In critical care environments like the intensive care unit or operating room environments, blood pressure can be continuously monitored with an arterial catheter inserted in the patient's radial or femoral artery. In one aspect, blood pressure can be measured intermittently using a pressured cuff and a technique called oscillometry. A vital sign monitor performs both the catheter and cuff-based measurements of blood pressure. Alternatively, blood pressure can be monitored continuously with a technique called pulse transit time, defined as the transit time for a pressure pulse launched by a heartbeat in a patient's arterial system. PTT has been shown in a number of studies to correlate to systolic, diastolic, and mean blood pressures. In one aspect, the blood pressure monitor can be coupled to a data communication device so that the results of a blood pressure analysis performed and stored by the meter can be reported directly to a monitoring facility that tracks the results and the patient's status.

It will be apparent to one skilled in the art that many other biometric and telehealth sensors may be incorporated into the sensor interface 480. For instance, SpO2 monitor (pulse oximetry) or body temperature sensor may also aid in forming a complete health profile of a subject patient. Further, body motion sensors or accelerometers worn on the body of the subject (or woven into the fabric of the clothing) can aid in determining the activity level of the subject patient. In another aspect, the sensors can be incorporated into an undergarment so that they are less noticeable and/or cumbersome and conform more closely to the user's body. In some aspects, sensors can be embedded in the skin of a user. The sensors 120 can gather data relating to the subject's form, balance, gait, speed, position, and/or stride. The sensors 120 can then send data to the sensor interface 480.

Figure 5:
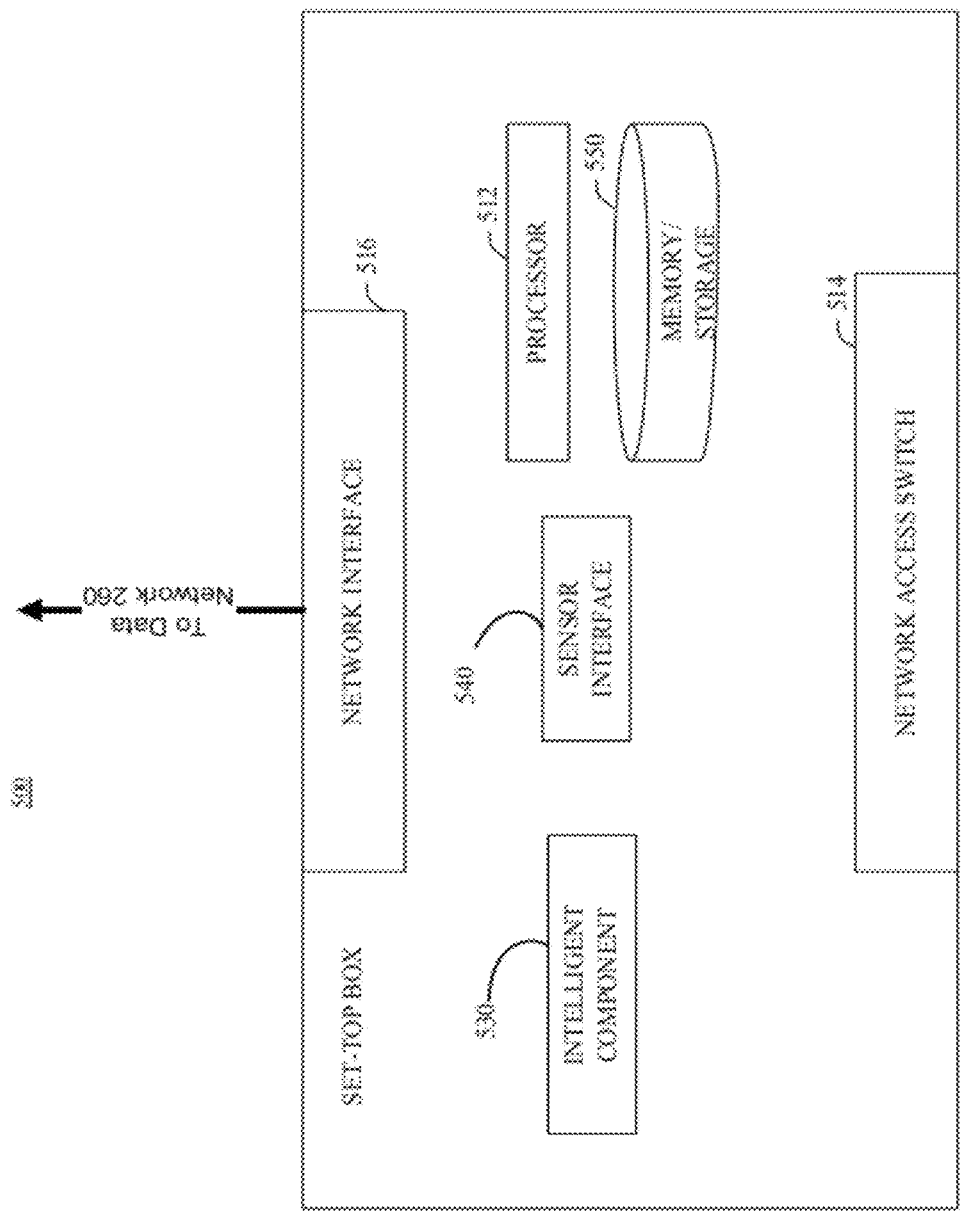
FIG. 5 is a simplified schematic illustrating an operating environment according to exemplary embodiments.

Referring to FIG. 5, there is shown a schematic illustration of a set-top box 500 in accordance with the principles of the various embodiments. The set-top box 500 includes an intelligent component 530, a sensor interface 540, a memory 550, a processor 512, a network access switch 514, and a network interface 516. The memory 510, in a particular embodiment, includes non-volatile memory.

The set-top box 500 generally provides broadband services including a voice telephony service, a high speed data service, a video service, other broadband service, or any combination thereof. In a particular aspect, the set-top box 500 communicates with a service provider using an Internet Protocol Television (IPTV) protocol through the network interface 516. In another particular aspect, the service provider uses a data-over-cable service interface specification (DOCSIS) protocol.

The set-top box 500 includes an intelligent component 530 which monitors all or substantially all biometric data gathered from the sensor interface 540. In one aspect, the intelligent component 530 executes a periodic check of the data gathered at the sensor interface 540 so that biometric data is collected and forwarded only if certain predefined threshold conditions are met. For instance, an otherwise healthy subject patient may be monitored only for certain cardiac events or for a certain threshold level of heart activity. In an alternative aspect, the intelligent component 530 forwards all of the sensor data collected at the sensor interface. In yet another aspect, the intelligent component forwards periodic summaries of sensor data collected at the sensor interface 540. In another aspect, the intelligent component 530 performs a rules-based analysis so that network outages or intermittent slowdowns at the service provider can be monitored. Upon detection of a network outage, the intelligent component 530 buffers the sensor data for later transmission.

The intelligent component 530, in an aspect, includes a heartbeat monitor or a specialized sensor (not shown) for monitoring the broadband connection. In one aspect, a residential gateway may wait a predetermined period of time after initial indications from the monitor or sensor before determining that the loss of connectivity has occurred. It will be noted that there should be consideration for intermittent losses of connectivity when there are periods with lack of packet transmissions and packet receptions. Additionally, there may be perceived an intermittent loss of connectivity when most or all of the connected devices for a residential gateway have been powered off.

Generally, the set-top box (STB) 500 receives encoded/compressed digital signals from the signal source (perhaps at the cable provider or telephone company TV provider's headend) and decodes/decompresses those signals, converting them into analog or digital signals that the television can understand. The STB 500 also accepts commands from the user (e.g., via the use of remote devices such as a remote control) and transmits these commands back to the network operator through a return path. Most set-top boxes 500 deployed today have return path capability for two-way communication.

The set-top box 500 transmits signals through a data network 260 such as the Internet. Coupled to the data network is a system management station 280 and a database 230 for monitoring the subject patient 210. The system management station 280 is also configured to provide various home health services to a subject patient located remotely from the system management station through the data network 260. In one or more aspect, it is contemplated that the system for monitoring of healthcare sensors may be configured to include additional system management stations 280. The additional system management stations 280 may be used to provide additional home health services such as monitoring by specialist physicians, ambulatory service providers, emergency medical personnel, nurse practitioners, and so forth. It is further contemplated that such additional provider and/or system management stations 280 may be used to provide backup home health services to a subject patient and/or management services for the integrated television-based broadband home health system. It is further contemplated that such additional provider and/or system management stations 280 may be used by medical service providers and/or family members of the subject patient to periodically monitor various characteristics of the subject patient in order to periodically "check up" on the subject patient.

The system management station 280 (in this case accessed via data network 260, or alternatively via data networks 160 or 340) may be a healthcare provider station where healthcare professionals are available to provide home healthcare services to patients remotely located. Generally, the system management station 280 would be located at either a physician's office or a healthcare agency or other type of organization responsible for providing home health services to patients at remotely located patient stations. In the case of a physician's office the system management station 280 would typically be comprised of a computer system, for example, a personal computer ("PC") having a plurality of peripheral devices coupled thereto. Software residing on the PC should include an Internet browser, for example, Microsoft Explorer, video conferencing software, for example, Microsoft NetMeeting, and any software applications needed for communicating with the subject patient. The software residing on the PC may also include various displays and interfaces so that videoconference calls can originate at either the set-top box 500 or at the system management station 280.

Figure 6:
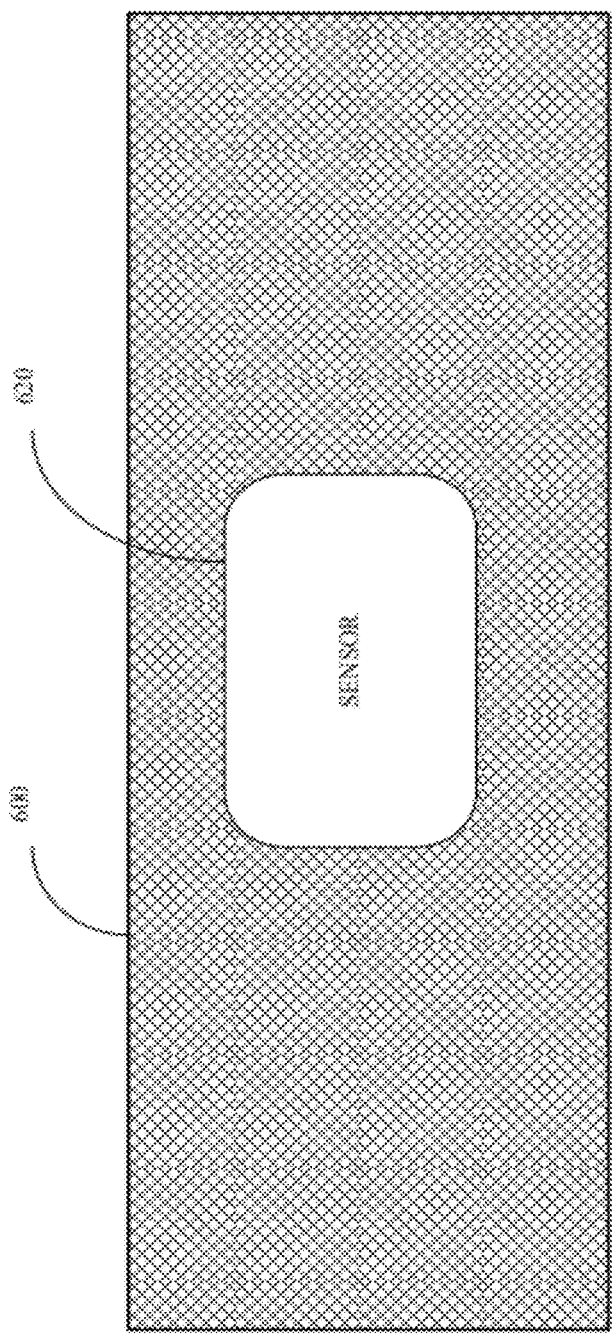
FIG. 6 is a simplified schematic illustrating a biometric sensor according to exemplary embodiments.

Referring now to FIG. 6, there is shown a sensor arrangement in accordance with an exemplary embodiment. Sensors 620 can be woven into the fabric of the clothing or apparel 600. In another aspect, the sensor 620 can be incorporated into an undergarment so they are less noticeable and/or cumbersome and conform more closely to the user's body. In another aspect, some sensors, such as the gait sensor, can be embedded into the soles of shoes or other footwear.

Figure 7:
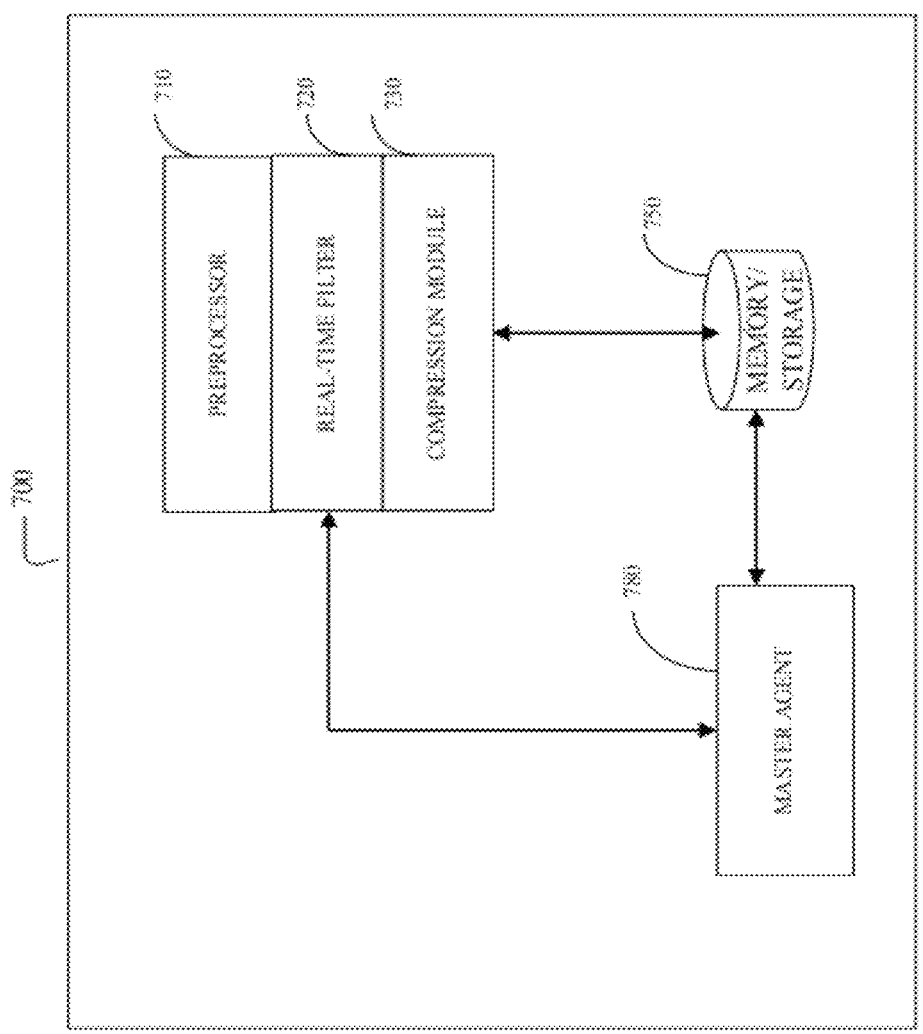
FIG. 7 is a simplified schematic illustrating a database engine according to exemplary embodiments.

Referring now to FIG. 7, there is shown a detailed schematic diagram of a system management station 700 in accordance with an exemplary embodiment. The system management station 700 includes a memory/storage 750 which acts as a database. The system management station 700 further includes a preprocessor 710, real-time filter 720, a compression module 730, and a master agent 780. The preprocessor 710 first receives the data so that various noises are removed from the data resulting in a data with a higher signal to noise ratio. In one aspect, the preprocessor 710 extracts identifiable features from the data so that windowing, sub-band transformation, mean extraction, and re-sampling may be prioritized in the extraction of data from the signal.

The real-time filter 720 then extracts or filters out data that may be necessary for archival or historical purposes from the necessary data for real-time analysis. In one aspect, the real-time filter 720 produces a result, which can be based on the entire record, or based on a portion of the entire record including, e.g., access records that are typically not applied in subject patient monitoring. For example, if the subject patient is suffering from diabetes, pulse monitoring data may not be authorized or may even be inappropriate for analysis by a healthcare professional. The real-time filter 720 applies access rules so that unauthorized data is not accessible to inappropriate personnel. In another aspect, the filter applies rule validation and administration for firewalls. Filter rules on a firewall between a secure computer network and a nonsecure computer network are validated from a user interface. A user interface is presented in which a test packet can be defined. The user interface includes controls for defining values for attributes of the test packet, wherein the attributes of the test packet are selected from a set of attributes of normal packets normally sent between the secure and nonsecure computer networks. A defined test packet is validated against a set of filter rules in the firewall or matched against the filter rules to determine those filter rules with matching attributes to the defined packet. When validating responsive to the failure of the test packet in the validating step, the filter rule in the set of filter rules that denied the test packet is displayed. The results can then be filtered based on the defined rules.

The sensor data is then transmitted to the compression module 730. The compression module 730, in one aspect, applies a data compression/decompression scheme using a passive data storage media for storage of biometric and telehealth sensor data information. The system operates on central processing hardware so that efficient storage and retrieval of information may be provided.

The memory/storage 750 acts as a database for a highly structured data storage which provides for transmission, use and security protection of the data. In one aspect, the database is a key management system where a plurality of keys are stored in a secure key database. A user authentication, such as a biometric authentication, is used to access the secure key database. Often the database is encrypted with a key that is accessible through user authentication.

In another aspect, the memory/storage 750 is a biometric and biomechanical data services provider (e.g., the provider of the sensors, the operator of a website, the server, the storage systems, and the database) can collect, store, and mine any of the acquired biometric data for any suitable instructional, health-related, marketing, promotional, advertising, or business objective. The biometric data can be shared among doctors, trainers, and health professionals to develop new methods to prevent or reduce injury or to help improve recovery from injury. It will be apparent that many types of devices and many wired and wireless channels of communication are possible to share biometric and biomechanical data derived from one or more sensors 120 among various users, learning centers, websites, etc. Many uses are possible and the examples discussed herein are intended to be illustrative and non-limiting.

The master agent 780 provides feedback to the subject patient and may act as a "virtual" doctor or health professional. In the absence of a human doctor or healthcare professional (or as a supplement thereto), the master agent 780 analyzes the sensor data and provides statistical analysis and real-time feedback to the subject patient. As just one example, the master agent 780 collects sensor data from multiple subjects or multiple users and processes that data to find patterns or establish norms. In some aspects, the master agent 780 can include rules based analysis so that a particular subject patient's medications or medical history is analyzed and compared to other medications and medical histories. As a further example, the master agent 780 can monitor a subject patient's vital signs in real time by monitoring sensor data captured and can be wirelessly transmitted to a trainer display system. As used herein, the term "real time" is used broadly to mean that the data is not available hours later, but is instead available within less than one hour. In a preferred aspect, the monitoring and some analysis can be done substantially instantaneously. Advantageously, high-speed data transfer can allow monitoring to occur within a short time (e.g., less than 5 minutes) of the sensor data collection. In some aspects, monitoring can occur within less than one minute of the body movement. In one aspect, all data is stored so that analysis of that data can be compared to other athletes, e.g., to enhance the training programs. Furthermore, a central network monitoring authority can be automatically alerted.

In one aspect, the master agent 780 may incorporate a graphical user interface ("GUI") through a profiling application running on a processor, such as part of a computer system of a user device and/or as provided by a system management station, such as a web-based server hosting the profiling application. The provided visual environment may be displayed by the processor on a display device of the user device. The subject patient may interact with the visual environment by providing a number of inputs to change the size of a selected tag.

A GUI is a type of user interface which allows a user to interact with electronic devices such as computers, handheld devices, household appliances, office equipment and the like. GUIs are typically used to render visual and textual images which describe various visual metaphors of an operating system, an application, etc., and implemented on a processor/computer including rendering on a display device. Furthermore, GUIs can represent programs, files and operational functions with graphical images, objects, or virtual representations. The graphical images can include windows, fields, dialog boxes, menus, icons, buttons, cursors, scroll bars, maps, etc. Such images can be arranged in predefined layouts, or can be created dynamically (by the device itself or by a web-based server) to serve the specific actions being taken by a subject patient. In general, the user can select and/or activate various graphical images in order to initiate functions and tasks associated therewith. As just one example, a subject patient can select a button that opens, closes, minimizes, or maximizes a window, or an icon that launches a particular program. By way of another example, the GUI may present a typical user interface including a windowing environment and as such, may include menu items, pull-down menu items, pop-up windows, etc., that are typical of those provided in a windowing environment, such as may be represented within a Windows™. Operating System GUI as provided by Microsoft Corporation and/or an OS Operating System GUI, such as provided on an iPhone™, MacBook™, iMac™, etc., as provided by Apple, Inc., and/or another operating system.

In the description hereafter, a GUI displaying a tag cloud will be referred to as a tag cloud GUI or in short a tag cloud interface. As described hereafter, the present method may be implemented through a profiling application that is either web-based or resident on a user device. A web-based profiling application may be used to remotely contribute to the rendering of a tag cloud GUI. Furthermore, the contribution may comprise the rendering of the GUI itself (the user device handling the display) or the rendering may be generated locally on the device (profiling information describing the user profile is provided by the web-based profiling application to the user device for subsequent rendering). For a resident profiling application, the user profile as well as the tag cloud GUI are generated locally on the user device.

The GUI displays analyzed sensor data and may provide a graphical evaluation of the subject patient's vital signs with graphs, numbers, graphical depictions, charts, histograms, etc. The performance evaluation can include statistical analyses that, for example, determine the subject patient's average vital signs and comparisons to similar patients with similar demographics and the patient's deviations from this average. For example, statistical techniques can be used to compare the patient's vital signs with other patients as defined by demographics, geography, general fitness level, and the like.

In some aspects, the data storage services provided by the system management station includes storing health-related data collected from or otherwise provided by the patient located at the patient station. For example, the health-related data may include data acquired by one or more electronic devices used to measure the vital signs or other health indices of the patient, answers to the questions contained in one or more questionnaires electronically filled out by the patient, and responses to system and medication reminders for compliance monitoring. The database management services provided by the system management station includes the scheduling of healthcare, caregiver and/or educational sessions for a subject patient and the scheduling of data collection times at which the vital signs and/or other health indices of a patient are to be measured. The database management services provided by the system management station further may include the scheduling of an appropriate type and number of reminders to be issued in connection with each scheduled session and/or data collection time. In another aspect, the system management station may provide security services so that access to sensitive patient information is selectively controlled. The security services include controlling access to electronic patient records and other confidential information maintained in the databases, controlling the establishment of connections between a physician or other healthcare professional requesting initiation of a telemedicine or telehealth session between the system management station and the set-top box and controlling the establishment of connections between a family member or other persons.

Telehealth services which may be provided to a subject patient associated with the set-top box may also include various types of education services. For example, the system management station may stream instructional videos over the data network to the set-top box, either upon receipt of a request by the subject patient or by the physician or other healthcare professional. Variously, the educational videos may be streamed on demand or at a pre-arranged time scheduled in advance. It is further contemplated that the educational services provided by the system management station may include interactive educational services, either upon receipt of a request by the subject patient or by the physician or other healthcare professional.

In another aspect, the system management station manages a reminder service. The reminder services provided by the system management station may issue medication reminders intended to remind the patient to take prescription or non-prescription medications or system reminders intended to remind the patient: (1) to measure their vital signs or other indices of their health using various sensor devices; (2) of an upcoming telemedicine or telehealth session with a physician or other health care professional; (3) of an upcoming remote caregiving session with a family member or other caregiver; or (4) of an upcoming telehealth session being broadcast by the system management station.

The reminders issued by the reminder service of the system management station may either be of a first type which requires a response or acknowledgement or of a second type which does not require a response or acknowledgement. If an immediate response to the first type of reminder is not convenient, the patient can temporarily reset the reminder for reissuance after a pre-determined period of time. If the subject patient fails to reset, respond or otherwise acknowledge a reminder requiring a response or acknowledgement, the system management station may notify an emergency services provider of a potential emergency condition. Conversely, reminders which do not require a response from the subject patient are typically configured to be broadcast for a predetermined period of time. At the conclusion of the broadcast, the reminder is typically repeated, either immediately or after a pre-determined time period. The reminder is typically repeated for a pre-determined number of times and then ends.

In conjunction with the reminder service, the system management station maintains compliance records which may be periodically retrieved, for example, by a physician or other healthcare professional to determine the subject patient's compliance with the various reminders issued by the reminder service of the system management station. Typically, the compliance records will maintain a list of the date, time and type of all reminders issued by the system management station. The compliance records will also maintain the patient's responses and/or failures to respond to those reminders.

In one aspect, the subject patient may access the biometric data from the sensors concurrent with the transmission to the system management station. Therefore, in some aspects, the subject can gather physiological and/or biometric data using the sensors, send that data to the set-top box which in turn transmits the data to the system management station. The subject can then become a user of the biometric data by accessing the data from the set-top box. It is contemplated that the subject can view or interact with the data in a variety of formats. For example, in one aspect, the primary feedback method to the subject is auditory. The wireless link would use speech synthesis to create a "narrative" of data, progress, and warnings (e.g. high-pulse rate). This notification function can also provide "reassurance" that the network is functional and is collecting/analyzing data (e.g., a periodic "beep" indicating that data is being received by the database/analyzer). In another example, the user can view three-dimensional animations, histograms, or other graphical reports of the subject patient's vital signs. As a further example, the subject patient can view the data in a tabular format so that the data may be compared to the subject's past performance metrics (for e.g., against the subject patient in similar environmental conditions, or the like). As a further example, the subject can view the data in a tabular format so that the data may be compared to metrics observed in other subject patients' performances.

Various other analyses of the subject patient's vital signs and health indicators are contemplated. For example, applications may include a custom menu interface. The custom menu interface may allow a subject patient or a physician or other healthcare professional to customize the interface so that specialized healthcare related sensor data may utilize more advanced (or simplified) interfaces, e.g., dependent upon the users' cognitive abilities, familiarity, and/or interactive specificity. This menu may include interactive queries or solicit information regarding the user's daily goals, subjective opinions or overall impression of the activity and one's performance which could be incorporated in the Motivation Index described below.

Various other Report Generation Tools and Templates are also contemplated. XML, HTML or other authoring language used to create documents on the Web that would provide an interactive browser-based user interface to access additional performance data analysis and report generation tools and templates that may not be available or offered with the standard product.

As a further example, a Range of Motion (ROM) Pattern Generator provides key control points to be captured along the desired trajectory and stored in order that the algorithm can calculate an optimally smooth path, in real-time, during the comparative analysis phase. A further example is a ROM Pattern Capture & Replay so that the athlete can replay the performance. The ROM pattern can be can saved to memory in real-time by discrete position samples versus time depending upon the resolution desired and memory limitations and later played back on the transponder or remote display for analysis.

It is contemplated that other Activity Specific Attributes, including Reps/Sets, Duration, Pause, Heart Rate Limits, intra-activity delay, level, point scalars, energy expenditure, task-oriented triggers, etc., and other parametric data that controls intensity, execution rate and scoring criteria for the activity may also be measured and analyzed.

Figure 8:
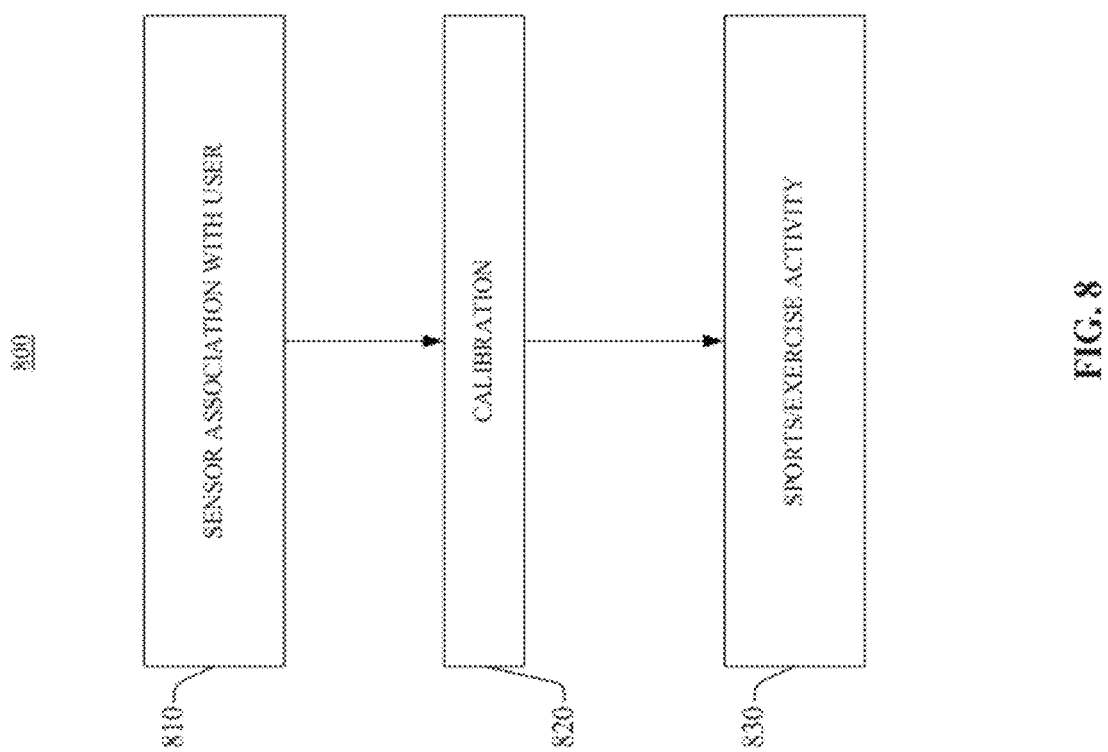
FIG. 8 is a flowchart illustrating the example steps according to exemplary embodiments.

FIG. 8 is a flowchart of an example method 800 for initializing the sensor arrangement at the commencement of biometric or telehealth sensor monitoring. At 810, the sensor is associated with the user. In one aspect, the step can include the authenticating of various sensors (mating of a sensor with a sensor interface) so that sensors transmit data to the appropriate sensor interface. In one aspect, for a transceiver utilizing the Zigbee communication protocol, the sensors can be mated to the Zigbee controller. At 820, the sensors are calibrated for proper performance. Calibration typically varies by the type of sensor device to be calibrated. For instance, some sensors dictate sensor accuracy and provide tight tolerances and some sensors are simply factory calibrated. At 830, the subject patient may begin any physical activity (or sports or exercise activity).

Figure 9:
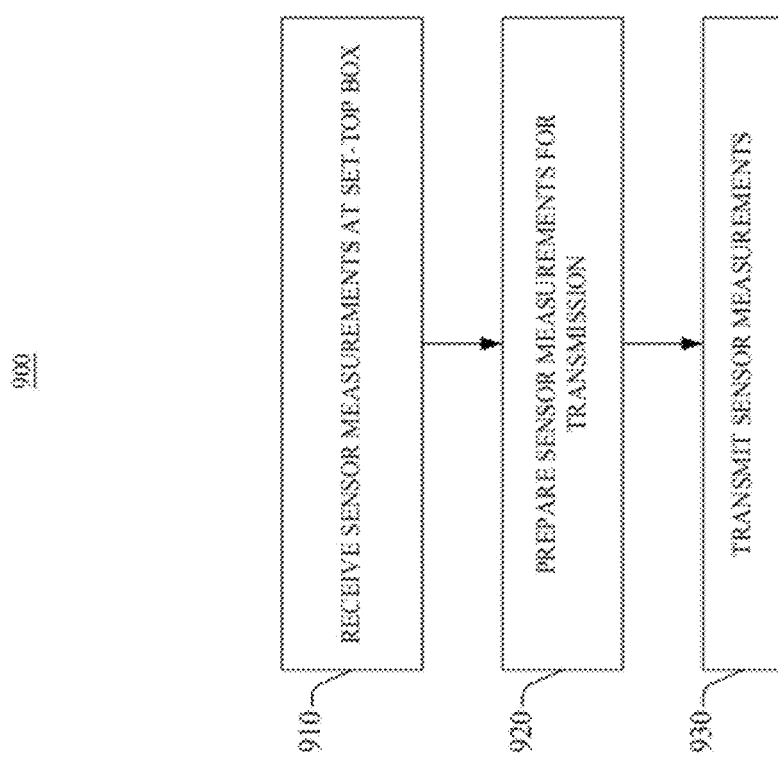
FIG. 9 is a flowchart illustrating the example steps according to exemplary embodiments.

FIG. 9 is a flowchart example of a method 900 for set-top box data transmission. At 910, the set-top box receives sensor measurements. At 920, the set-top box prepares the sensor measurements for transmission. The set-top box can collect and store data (e.g., analog and/or digital data) from the sensors. In one aspect, the data is converted from analog to digital in the sensors or the set-top box to facilitate storage and/or transmittance. In another aspect, the data is sequenced, coded, and or separated to make the reception, storage, and/or transmission more efficient. At 930, the further processed sensor data is transmitted.

Figure 10:
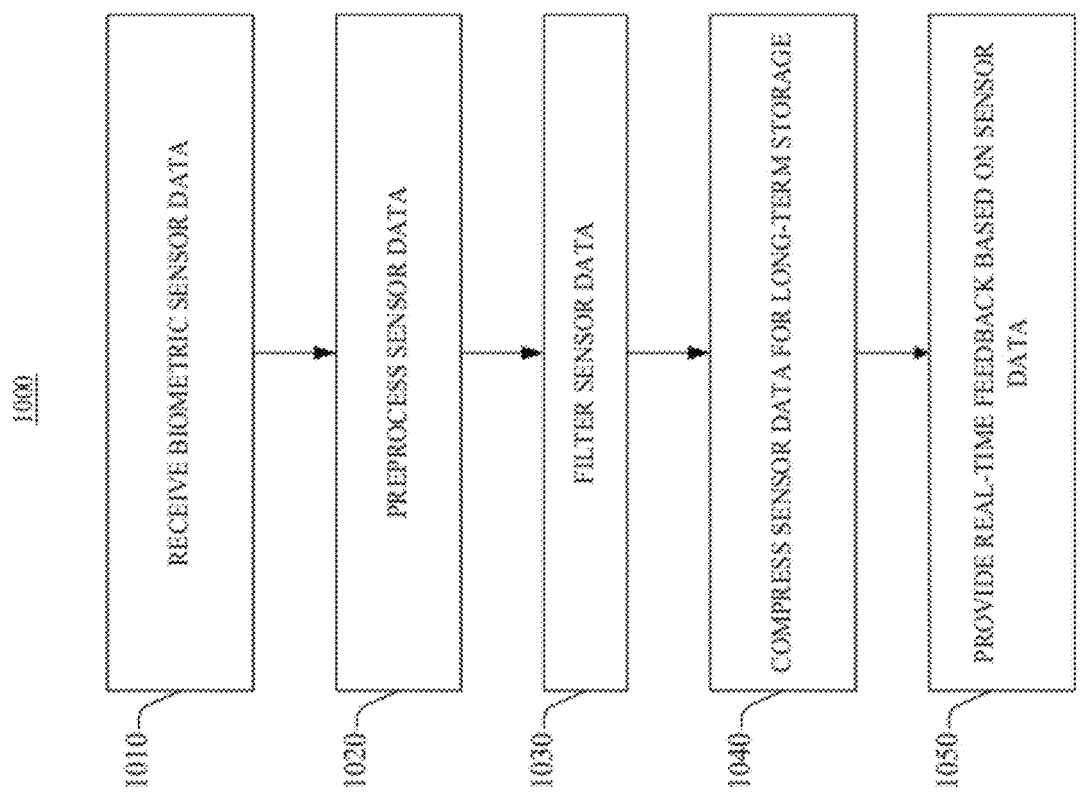
FIG. 10 is a flowchart illustrating the example steps according to exemplary embodiments.

FIG. 10 is a flowchart example of a method 1000 for receiving and analyzing sensor data at the system management station. At 1010, the system management station receives biometric sensor data. At 1020, the preprocessor receives the sensor data so that various noises are removed from the data resulting in a data with a higher signal to noise ratio. In one aspect, the preprocessor extracts identifiable features from the data so that windowing, sub-band transformation, mean extraction, and re-sampling may be prioritized in the extraction of data from the signal.

At 1030, the real-time filter extracts or filters out data that may be necessary for archival or historical purposes from the necessary data for real-time analysis. In one aspect, the filter produces a result, typically based on the entire record, based on access records which are typically not applied in subject patient monitoring. For example, if the subject patient is suffering from diabetes, pulse monitoring data may not be authorized or may even be inappropriate for analysis by a healthcare professional. The real-time filter applies access rules so that unauthorized data is not accessible to inappropriate personnel. In another aspect, the filter applies rule validation and administration for firewalls. Filter rules on a firewall between a secure computer network and a nonsecure computer network are validated from a user interface. A user interface is presented in which a test packet can be defined. The user interface includes controls for defining values for attributes of the test packet, where the attributes of the test packet are selected from a set of attributes of normal packets normally sent between the secure and nonsecure computer networks. A defined test packet is validated against a set of filter rules in the firewall or matched against the filter rules to determine those filter rules with matching attributes to the defined packet. When validating, responsive to the failure of the test packet in the validating step, the filter rule in the set of filter rules that denied the test packet is displayed. to the data is since the access rules are typically not applied within the custodian network. The results are then filtered based on the defined rules.

At 1040, the compression module compresses sensor data for long-term storage. The compression module, in one aspect, applies an efficient data compression/decompression scheme using a passive data storage media for storage of biometric or telehealth sensor data information. The system operates on central processing hardware so that efficient storage and retrieval of information may be provided.

At 1050, the master agent provides feedback to the athlete and acts as a "virtual" physician or healthcare professional. As discussed above, the master agent 780 provides feedback to the subject patient and may act as a "virtual" doctor or health professional. In the absence of a human doctor or healthcare professional (or as a supplement thereto), the master agent analyzes the sensor data instantaneously and provides statistical analysis and real-time feedback to the subject patient. As just one example, the master agent collects sensor data from multiple subjects or multiple users and processes that data to find patterns or establish norms. In some aspects, the master agent can include rules based analysis so that a particular subject patient's medications or medical history is analyzed and compared to other medications and medical histories. As a further example, the master agent can monitor a subject patient's vital signs in real time by monitoring sensor data captured and wirelessly transmitted to the trainer display system. As used herein, the term "real time" is used broadly to mean that the data is not available hours later, but is instead available within less than one hour. In a preferred aspect, the monitoring and some analysis can be done instantaneously. Advantageously, high-speed data transfer can allow monitoring to occur within a short time (e.g., less than 5 minutes) of the sensor data collection. In some aspects, monitoring can occur within less than one minute of the body movement. In one aspect, all data is stored so that analysis of that data can be compared to other athletes and enhance the training programs. automatically alerting a central network monitoring authority, with associated components is illustrated in accordance with aspects described herein.

In one aspect, the master agent 780 may incorporate a graphical user interface ("GUI") through a profiling application running on a processor, such as part of a computer system of a user device and/or as provided by a system management station, such as a web-based server hosting the profiling application. The provided visual environment may be displayed by the processor on a display device of the user device. The subject patient may interact with the visual environment by providing a number of inputs to change the size of a selected tag.

A GUI is a type of user interface which allows a user to interact with electronic devices such as computers, hand-held devices, household appliances, office equipment and the likes. GUIs are typically used to render visual and textual images which describe various visual metaphors of an operating system, an application, etc., and implemented on a processor/computer including rendering on a display device. Furthermore, GUIs can represent programs, files and operational functions with graphical images, objects, or virtual representations. The graphical images can include windows, fields, dialog boxes, menus, icons, buttons, cursors, scroll bars, maps, etc. Such images can be arranged in predefined layouts, or can be created dynamically (by the device itself or by a web-based server) to serve the specific actions being taken by a subject patient. In general, the user can select and/or activate various graphical images in order to initiate functions and tasks associated therewith. As just one example, a subject patient can select a button that opens, closes, minimizes, or maximizes a window, or an icon that launches a particular program. By way of another example, the GUI may present a typical user interface including a windowing environment and as such, may include menu items, pull-down menu items, pop-up windows, etc., that are typical of those provided in a windowing environment, such as may be represented within a Windows™. Operating System GUI as provided by Microsoft Corporation and/or an OS Operating System GUI, such as provided on an iPhone™, MacBook™, iMac™, etc., as provided by Apple, Inc., and/or another operating system.

In the description hereafter, a GUI displaying a tag cloud will be referred to as a tag cloud GUI or in short tag cloud interface. As described hereafter, the present method may be implemented through a profiling application either web-based or resident on a user device. A web-based profiling application may be used to remotely contribute to the rendering of a tag cloud GUI. Furthermore, the contribution may comprise the rendering of the GUI itself (the user device handling the display) or the rendering may be generated locally on the device (profiling information describing the user profile is provided by the web-based profiling application to the user device for subsequent rendering). For a resident profiling application, the user profile as well as the tag cloud GUI are generated locally on the user device.

The GUI displays analyzed sensor data and may provide a graphical evaluation of the subject patient's vital signs athlete's performance with graphs, numbers, graphical depictions, charts, histograms, etc. The performance evaluation can include statistical analyses that, for example, determine the subject patient's average vital signs and comparisons to similar patients with similar demographics and the patient's deviations from this average. For example, statistical techniques can be used to compare the patient's vital signs with other suitable patients as defined by demographics, geography, general fitness level, and the like.

In some aspects, the data storage services provided by the system management station includes storing health-related data collected from or otherwise provided by the patient located at the patient station. For example, the health-related data may include data acquired by one or more electronic devices used to measure the vital signs or other health indices of the patient, answers to the questions contained in one or more questionnaires electronically filled out by the patient, and responses to system and medication reminders for compliance monitoring. The database management services provided by the system management station includes the scheduling of healthcare, caregiver and/or educational sessions for a subject patient and the scheduling of data collection times at which the vital signs and/or other health indices of a patient are to be measured. The database management services provided by the system management station further may include the scheduling of an appropriate type and number of reminders to be issued in connection with each scheduled session and/or data collection time. In another aspect, the system management station may provide security services so that access to sensitive patient information is selectively controlled. The security services include controlling access to electronic patient records and other confidential information maintained in the databases, controlling the establishment of connections between a physician or other healthcare professional requesting initiation of a telemedicine or telehealth session between the system management station and the set-top box and controlling the establishment of connections between a family member or other persons.

Telehealth services which may be provided to a subject patient associated with the set-top box may also include various types of education services. For example, the system management station may stream instructional videos, over the data network to the set-top box, either upon receipt of a request by the subject patient or by the physician or other healthcare professional. Variously, the educational videos may be streamed on demand or at a pre-arranged time scheduled in advance. It is further contemplated that the educational services provided by the system management station may include interactive educational services, again either upon receipt of a request by the subject patient or by the physician or other healthcare professional.

In another aspect, the system management station manages a reminder service. The reminder services provided by the system management station may issue medication reminders intended to remind the patient to take prescription or non-prescription medications or system reminders intended to remind the patient: (1) to measure their vital signs or other indices of their health using various sensor devices; (2) of an upcoming telemedicine or telehealth session with a physician or other health care professional; (3) of an upcoming remote caregiving session with a family member or other caregiver; or (4) of an upcoming telehealth session being broadcast by the system management station.

The reminders issued by the reminder service of the system management station may either be of a first type which requires a response or acknowledgement or of a second type which does not require a response or acknowledgement. Of course, if an immediate response to the first type of reminder is not convenient, the patient can temporarily reset the reminder for reissuance after a pre-determined of time. If the subject patient fails to reset, respond or otherwise acknowledge a reminder requiring a response or acknowledgement, the system management station may notify an emergency services provider of a potential emergency condition. Conversely, reminders which do not require a response from the subject patient are typically configured to be broadcast for a predetermined period of time. At the conclusion of the broadcast, the reminder is typically repeated, either immediately or after a pre-determined time period. The reminder is typically repeated for a pre-determined number of times and then ends.

In conjunction with the reminder service, the system management station maintains compliance records which may be periodically retrieved, for example, by a physician or other healthcare professional to determine the subject patient's compliance with the various reminders issued by the reminder service of the system management station. Typically, the compliance records will maintain a list of the date, time and type of all reminders issued by the system management station. The compliance records will also maintain the patient's responses and/or failures to respond to those reminders.

In one aspect, the subject patient may access the biometric data from the sensors concurrent with the transmission to the system management station. Therefore, in some aspects, the subject can gather physiological and/or biometric data using the sensors, send that data to the set-top box which in turn transmits the data to the system management station. The subject can then become a user of the biometric data by accessing the data from at the set-top box. It is contemplated that the subject can view or interact with the data in a variety of formats. For example, in one aspect, the primary feedback method to the subject is auditory. The wireless link would use speech synthesis to create a "narrative" of data, progress, and warnings (e.g. high-pulse rate). This notification function can also provide "reassurance" that the network is functional and is collecting/analyzing data (e.g. a periodic "beep" indicating that data is being received by the database/analyzer). In another example, the user can view three-dimensional animations, histograms, or other graphical reports of the subject patient's vital signs. As a further example, the subject patient can view the data in a tabular format so that the data may be compared to the subject's past performance metrics (for e.g., against the subject patient in similar environmental conditions, or the like). As a further example, the subject can view the data in a tabular format so that the data may be compared to metrics observed in other subject patients' performances.

Various other analysis of the subject patient's vital signs and health indicators are contemplated. For example, applications may include a custom menu interface. The custom menu interfaces allow a subject patient or a physician or other healthcare professional to customize the interface so that specialized healthcare related sensor data may require more advanced (or simplified) interfaces dependent upon the users' cognitive abilities and interactive specificity. This menu may include interactive queries or solicit information regarding the user's daily goals, subjective opinions or overall impression of the activity and one's performance which could be incorporated in the Motivation Index described below.

Various other Report Generation Tools and Templates are also contemplated. XML, HTML or other authoring language used to create documents on the Web that would provide an interactive browser-based user interface to access additional performance data analysis and report generation tools and templates that may not be available or offered with the standard product.

As a further example, a Range of Motion (ROM) Pattern Generator provides key control points to be captured along the desired trajectory and stored in order that the algorithm can calculate an optimally smooth path, in real-time, during the comparative analysis phase. A further example is a ROM Pattern Capture & Replay so that the athlete can replay the performance. The ROM pattern can be can saved to memory in real-time by discrete position samples versus time depending upon the resolution desired and memory limitations and later played back on the transponder or remote display for analysis.

It is contemplated that other Activity Specific Attributes, including Reps/Sets, Duration, Pause, Heart Rate Limits, intra-activity delay, level, point scalars, energy expenditure, task-oriented triggers, etc., and other parametric data that controls intensity, execution rate and scoring criteria for the activity may also be measured and analyzed.

Figure 11:
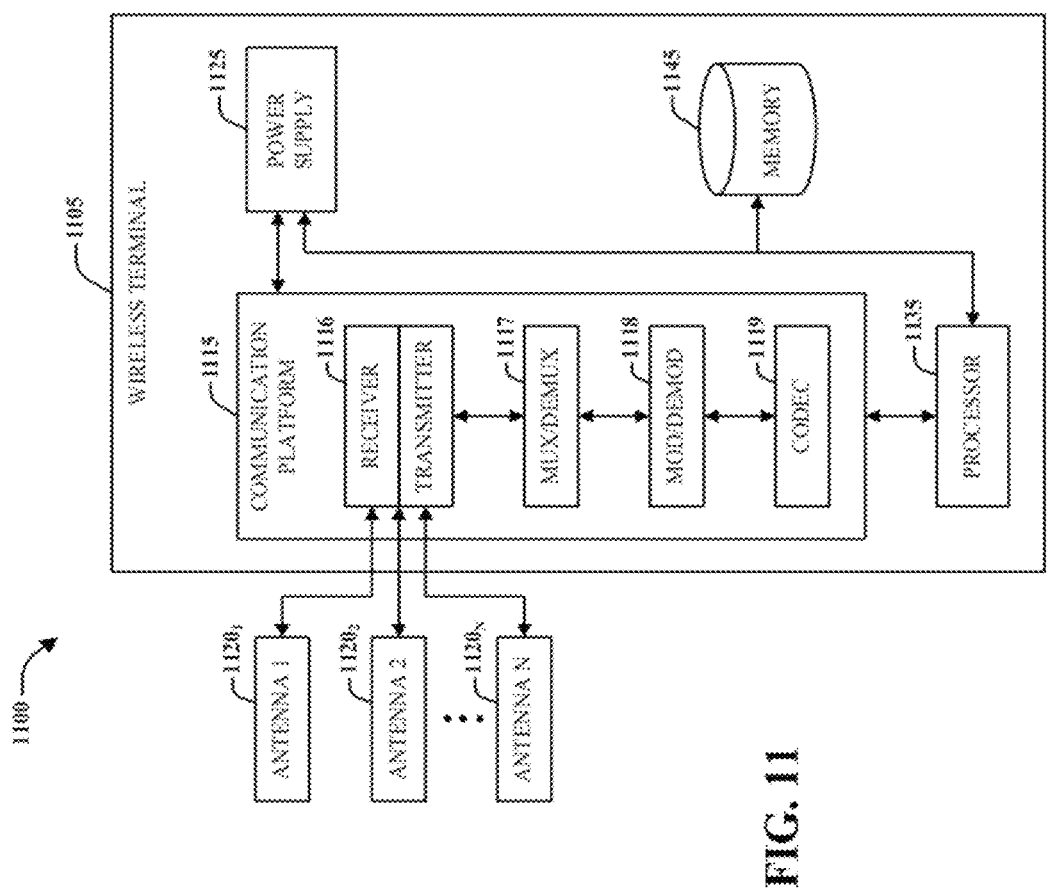
FIG. 11 illustrates an example network device that can be utilized to implement one or more of the various aspects described herein.

In order to provide further context for various aspects of the disclosed subject matter, FIG. 11 illustrates a non-limiting example system 1100 that can implement some or all of the aspects described herein. System 1100 can include a wireless terminal 1105. In an embodiment, wireless terminal 1105 can receive and transmit signal(s) to and/or from wireless devices such as femto access points, access terminals, wireless ports and routers, or the like, through a set of N antennas 1120. In one example, antennas 1120 can be implemented as part of a communication platform 1115, which in turn can comprise electronic components and associated circuitry and/or other means that provide for processing and manipulation of received signal(s) and signal(s) to be transmitted.

In an aspect, communication platform 1115 can include a receiver/transmitter or transceiver 1116, which can transmit and receive signals and/or perform one or more processing operations on such signals (e.g., conversion from analog to digital upon reception, conversion from digital to analog upon transmission, etc.). In addition, transceiver 1116 can divide a single data stream into multiple, parallel data streams, or perform the reciprocal operation.

In another example, a multiplexer/demultiplexer (mux/demux) unit 1117 can be coupled to transceiver 1116.

Mux/demux unit 1117 can, for example, facilitate manipulation of signal in time and frequency space. Additionally or alternatively, mux/demux unit 1117 can multiplex information (e.g., data/traffic, control/signaling, etc.) according to various multiplexing schemes such as time division multiplexing (TDM), frequency division multiplexing (FDM), orthogonal frequency division multiplexing (OFDM), code division multiplexing (CDM), space division multiplexing (SDM), or the like. In addition, mux/demux unit 1117 can scramble and spread information according to substantially any code generally known in the art, such as Hadamard-Walsh codes, Baker codes, Kasami codes, polyphase codes, and so on.

In a further example, a modulator/demodulator (mod/demod) unit 1118 implemented within communication platform 1115 can modulate information according to multiple modulation techniques, such as frequency modulation, amplitude modulation (e.g., N-ary quadrature amplitude modulation (N-QAM), etc.), phase-shift keying (PSK), and the like. Further, communication platform 1115 can also include a coder/decoder (codec) module 1119 that facilitates decoding received signal(s) and/or coding signal(s) to convey.

According to another aspect, wireless terminal 1105 can include a processor 1135 configured to confer functionality, at least in part, to substantially any electronic component utilized by wireless terminal 1105. As further shown in system 1100, a power supply 1125 can attach to a power grid and include one or more transformers to achieve a power level at which various components and/or circuitry associated with wireless terminal 1105 can operate. In one example, power supply 1125 can include a rechargeable power mechanism to facilitate continued operation of wireless terminal 1105 in the event that wireless terminal 1105 is disconnected from the power grid, the power grid is not operating, etc.

In a further aspect, processor 1135 can be functionally connected to communication platform 1115 and can facilitate various operations on data (e.g., symbols, bits, chips, etc.), which can include, but are not limited to, effecting direct and inverse fast Fourier transforms, selection of modulation rates, selection of data packet formats, inter-packet times, etc. In another example, processor 1135 can be functionally connected, via a data or system bus, to any other components or circuitry not shown in system 1100 to at least partially confer functionality to each of such components.

As additionally illustrated in system 1100, a memory 1145 can be used by wireless terminal 1105 to store data structures, code instructions and program modules, system or device information, code sequences for scrambling, spreading and pilot transmission, location intelligence storage, determined delay offset(s), over-the-air propagation models, and so on. Processor 1135 can be coupled to the memory 1145 in order to store and retrieve information necessary to operate and/or confer functionality to communication platform 1115 and/or any other components of wireless terminal 1105.

Figure 12:
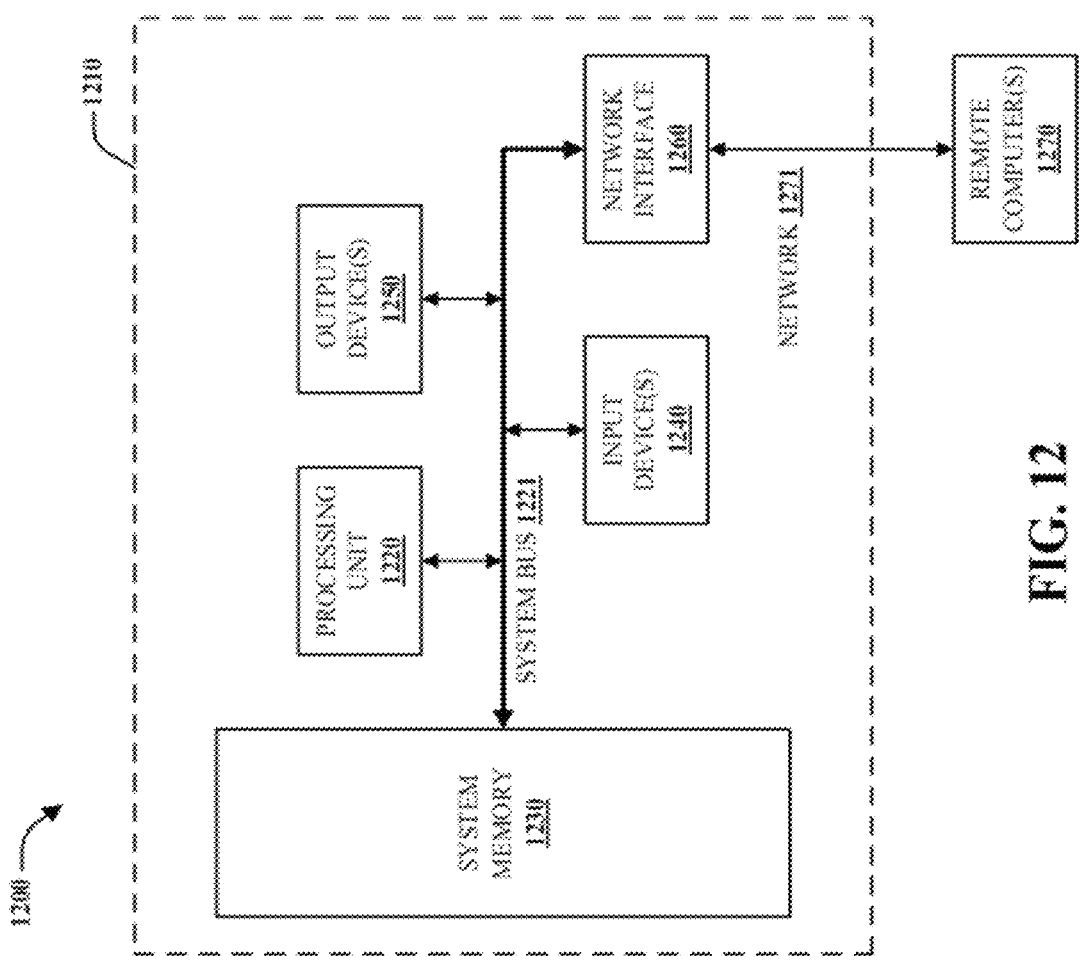
FIG. 12 illustrates an example computing architecture that is operable to execute various aspects described herein.

Turning to FIG. 12, a non-limiting example computing system or operating environment in which various aspects of the disclosed subject matter may be implemented is illustrated. One of ordinary skill in the art can appreciate that handheld, portable and other computing devices and computing objects of all kinds are contemplated for use in connection with the disclosed subject matter, e.g., anywhere that a communications system may be desirably configured. Accordingly, the below general purpose remote computer described below in FIG. 12 is but one example of a computing system in which the disclosed subject matter may be implemented.

Although not required, various aspects of the disclosed subject matter can partly be implemented via an operating system, for use by a developer of services for a device or object, and/or included within application software that operates in connection with the component(s) of the disclosed subject matter. Software may be described in the general context of computer-executable instructions, such as program modules, being executed by one or more computers, such as client workstations, servers or other devices. Those skilled in the art will appreciate that various aspects of the disclosed subject matter may be practiced with other computer system configurations and protocols.

FIG. 12 thus illustrates an example of a suitable computing system environment 1200 in which various aspects of the disclosed subject matter may be implemented, although as made clear above, the computing system environment 1200 is only one example of a suitable computing environment for a media device and is not intended to suggest any limitation as to the scope of use or functionality of the disclosed subject matter. Neither should the computing environment 1200 be interpreted as having any dependency or requirement relating to any one or combination of components illustrated in the example operating environment 1200.

With reference to FIG. 12, an example of a computing environment 1200 for implementing various aspects of the disclosed subject matter includes a general purpose computing device in the form of a computer 1210. Components of computer 1210 can include, but are not limited to, a processing unit 1220, a system memory 1230, and a system bus 1221 that couples various system components including the system memory to the processing unit 1220. The system bus 1221 can be any of several types of bus structures including a memory bus or memory controller, a peripheral bus, and a local bus using any of a variety of bus architectures.

Computer 1210 can include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, Electrically Erasable Programmable ROM (EEPROM), flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

The system memory 1230 can include computer storage media in the form of volatile and/or nonvolatile memory such as read only memory (ROM) and/or random access memory (RAM). A basic input/output system (BIOS), containing the basic routines that help to transfer information between elements within computer 1210, such as during start-up, can be stored in memory 1230. Memory 1230 typically also contains data and/or program modules that are immediately accessible to and/or presently being operated on by processing unit 1220. By way of example, and not limitation, memory 1230 can also include an operating system, application programs, other program modules, and program data.

The computer 1210 can also include other removable/non-removable, volatile/nonvolatile computer storage media. For example, computer 1210 could include a hard disk drive that reads from or writes to non-removable, nonvolatile magnetic media, a magnetic disk drive that reads from or writes to a removable, nonvolatile magnetic disk, and/or an optical disk drive that reads from or writes to a removable, nonvolatile optical disk, such as a CD-ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM and the like. A hard disk drive is typically connected to the system bus 1221 through a non-removable memory interface such as an interface, and a magnetic disk drive or optical disk drive is typically connected to the system bus 1221 by a removable memory interface, such as an interface.

A user can enter commands and information into the computer 1210 through input devices such as a keyboard and pointing device, commonly referred to as a mouse, trackball or touch pad. Other input devices can include a microphone, joystick, game pad, satellite dish, scanner, or the like. These and other input devices are often connected to the processing unit 1220 through user input 1240 and associated interface(s) that are coupled to the system bus 1221, but can be connected by other interface and bus structures, such as a parallel port, game port or a universal serial bus (USB). A graphics subsystem can also be connected to the system bus 1221. A monitor or other type of display device is also connected to the system bus 1221 via an interface, such as output interface 1250, which can in turn communicate with video memory. In addition to a monitor, computers can also include other peripheral output devices such as speakers and a printer, which can be connected through output interface 1250.

The computer 1210 can operate in a networked or distributed environment using logical connections to one or more other remote computers, such as remote computer 1270, which can in turn have media capabilities different from device 1210. The remote computer 1270 can be a personal computer, a server, a router, a network PC, a peer device or other common network node, or any other remote media consumption or transmission device, and can include any or all of the elements described above relative to the computer 1210. The logical connections depicted in FIG. 12 include a network 1271, such local area network (LAN) or a wide area network (WAN), but can also include other networks/buses. Such networking environments are commonplace in homes, offices, enterprise-wide computer networks, intranets and the Internet.

When used in a LAN networking environment, the computer 1210 is connected to the LAN 1271 through a network interface or adapter. When used in a WAN networking environment, the computer 1210 typically includes a communications component, such as a modem, or other means for establishing communications over the WAN, such as the Internet. A communications component, such as a modem, which can be internal or external, can be connected to the system bus 1221 via the user input interface of input 1240, or other appropriate mechanism. In a networked environment, program modules depicted relative to the computer 1210, or portions thereof, can be stored in a remote memory storage device. It will be appreciated that the network connections shown and described are exemplary and other means of establishing a communications link between the computers can be used.

It is to be noted that aspects, features, and/or advantages of the disclosed subject matter can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

Various aspects or features described herein can be implemented as a method, apparatus, system, or article of manufacture using standard programming or engineering techniques. In addition, various aspects or features disclosed in the subject specification can also be realized through program modules that implement at least one or more of the methods disclosed herein, the program modules being stored in a memory and executed by at least a processor. Other combinations of hardware and software or hardware and firmware can enable or implement aspects described herein, including disclosed method(s).

Computing devices typically include a variety of media, which can include computer-readable storage media or communications media, which two terms are used herein differently from one another as follows.

Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

What has been described above includes examples of systems and methods that provide advantages of the disclosed subject matter. It is, of course, not possible to describe every conceivable combination of components or methodologies for purposes of describing the disclosed subject matter, but one of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A multimedia delivery device, comprising:
    a network interface device configured to connect to a data network device of a communication network and to receive, via the data network device, a multimedia signal;
    a decoding device configured to decode the multimedia signal to produce a decoded signal and to provide the decoded signal to a display device;
    a sensor interface device coupled to the network interface device, wherein the sensor interface device is configured to interface with a sensor that gathers biometric data;
    a processor; and
    a memory that stores executable instructions that, when executed by the processor, facilitate performance of operations, comprising:
        monitoring, by the multimedia delivery device, the biometric data received from the sensor;
        determining, by the multimedia delivery device, that a defined threshold condition of the biometric data has been satisfied based on the monitoring;
        associating, by the multimedia delivery device, the biometric data with a subject identity in response to the determining that the defined threshold condition of the biometric data has been satisfied;
        generating summary data representative of a summary of at least a portion of the biometric data that satisfies the defined threshold condition;
        determining, by the multimedia delivery device, whether a network outage condition associated with the data network device of the communication network exists; and
        conditionally storing, by the multimedia device, the summary data when the network outage condition is determined to exist.

2. The multimedia delivery device of claim 1, wherein the operations further comprise:
    performing, by the multimedia delivery device, a calibration process that calibrates the sensor; and
    facilitating, by the multimedia delivery device, transmission of the summary data via the network interface device to another device in response to the determining that the defined threshold condition of the biometric data has been satisfied.

3. The multimedia delivery device of claim 2, wherein the operations further comprise:
    determining, by the multimedia device, that the network outage condition no longer exists; and
    facilitating the transmission of the summary data in response to the determining that the network outage condition no longer exists.

4. The multimedia delivery device of claim 2, wherein the facilitating the transmission of the summary data further comprises facilitating transmission of the summary data according to a defined schedule.

5. The multimedia delivery device of claim 1, wherein the sensor is a medication dispenser that monitors a medication parameter associated with the subject identity.

6. The multimedia delivery device of claim 1, wherein the sensor is a gait sensor that monitors a gait parameter associated with the subject identity.

7. The multimedia delivery device of claim 1, wherein the sensor is a pulse oximeter that monitors a pulse parameter associated with the subject identity.

8. The multimedia delivery device of claim 1, wherein the sensor interface device is configured to communicate using a Zigbee protocol.

9. The multimedia delivery device of claim 1, wherein the operations further comprise directing feedback information to a device of the subject identity based on a defined rule.

10. The multimedia delivery device of claim 9, wherein the defined rule relates to a determined state associated with the data network device of the communication network.

11. The multimedia delivery device of claim 1, wherein the sensor is a body weight scale that monitors a weight parameter associated with the subject identity, a heart rate monitor that monitors a heart parameter associated with the subject identity, or a glucometer that monitors a blood-sugar parameter associated with the subject identity.

12. The multimedia delivery device of claim 1, wherein the operations further comprise:
facilitating storing of the biometric data from the sensor for a defined time period; and
facilitating transmission of the biometric data after a second defined time period.

13. A method, comprising:
interfacing, by a multimedia delivery system comprising a processor and a sensor interface, to a telehealth sensor that gathers biometric data, wherein the multimedia delivery system facilitates presentation, to a display device, of media content received from a media content provider via a network device of a communication network;
processing, by the multimedia delivery system, the biometric data from the telehealth sensor to determine that a value for the biometric data satisfies a defined threshold condition;
associating, by the multimedia delivery system, the biometric data from the telehealth sensor with a subject identity in response to determining that the value for the biometric data meets the defined threshold condition;
generating, by the multimedia delivery system, summary data representative of a summary of at least a portion of the biometric data that satisfies the defined threshold condition;
conditionally storing, by the multimedia delivery system, the summary data in response to the condition that a network outage condition has been determined to exist; and
transmitting, by the multimedia delivery system, the summary data to a device associated with a healthcare provider identity in response to determining that the value for the biometric data satisfies the defined threshold condition.

14. The method of claim 13, wherein the operations further comprise performing, by the multimedia delivery system, a calibration process that calibrates the telehealth sensor.

15. The method of claim 13, wherein the interfacing comprises interfacing to a medication dispenser that monitors a medication parameter associated with the subject identity.

16. The method of claim 13, wherein the interfacing comprises:
interfacing comprises interfacing to a heart rate monitor that monitors a heart parameter associated with the subject identity; or
interfacing to a body weight scale that monitors a weight parameter associated with the subject identity.

17. A method, comprising:
interfacing, by a media device comprising a processor and a sensor interface, to a telehealth sensor that collects biometric data, wherein the media device is configured to present, to a display device, media content received from a media content provider device associated with a media content provider identity via a network device;
determining, by the media device, whether a data value for the biometric data has satisfied a defined condition;
generating, by the media device, summary data indicative of a summary of at least a portion of the biometric data that relates to the defined condition being satisfied;
associating, by the media device, the biometric data from the telehealth sensor with an identity in response to the defined condition being determined to have been satisfied;
conditionally storing, by the media device, the summary data in response to the condition that a network outage condition is determined to exist; and
transmitting, by the media device, the summary data to a healthcare provider device associated with a healthcare provider identity in response to the defined condition being determined to have been satisfied.

18. The method of claim 17, wherein the media device is a set-top box device.

19. The method of claim 18, wherein the operations further comprise performing, by the media device, a calibration process that calibrates the telehealth sensor.

20. The method of claim 18, wherein the interfacing comprises:
interfacing to a gait sensor that monitors a gait parameter associated with the identity; or
interfacing to a pulse oximeter that monitors a pulse parameter associated with the identity.

* * * * *